(12) United States Patent
Hitomi et al.

(10) Patent No.: US 6,313,267 B1
(45) Date of Patent: Nov. 6, 2001

(54) CALCIUM-BINDING PROTEINS

(75) Inventors: Jiro Hitomi; Ken Yamaguchi; Tokujiro Yamamura, all of Tokyo; Tatsuji Kimura, Saitama, all of (JP)

(73) Assignee: Advanced Life Science Institute, Inc., Saitama (JP)

( * ) Notice: Subject to any disclaimer, the term of this patent is extended or adjusted under 35 U.S.C. 154(b) by 0 days.

(21) Appl. No.: 09/270,455

(22) Filed: Mar. 17, 1999

Related U.S. Application Data

(62) Division of application No. 08/568,310, filed on Dec. 6, 1995, now Pat. No. 5,976,832.

(30) Foreign Application Priority Data

Mar. 6, 1995 (JP) ....................................... 7-45564
Mar. 6, 1995 (JP) ....................................... 7-70468

(51) Int. Cl.⁷ ............................. C07K 1/00; C12P 21/06
(52) U.S. Cl. ..................... 530/350; 530/350; 435/69.1; 435/69.7; 435/320.1; 435/252.3; 435/69.5; 435/325; 536/23.5

(58) Field of Search ................. 435/69.7, 320.1, 435/252.3, 69.1, 69.5, 325; 530/350; 536/23.5

(56) References Cited

U.S. PATENT DOCUMENTS 5,288,623 * 2/1994 Zenno et al. ................. 435/69.1

OTHER PUBLICATIONS

Dell'Angelica et al., The Journal of Biological Chemisty, vol. 269, No. 46, pp. 28929–28936, 1994.*
Guignard et al. Biochemical Journal, vol. 309, pp. 395–401, 1995.*
Alignments: Accession No. A55406, Dell'Angelica, 1994.*

* cited by examiner

*Primary Examiner*—Karen Cochrane Carlson
*Assistant Examiner*—Hope A. Robinson
(74) *Attorney, Agent, or Firm*—Anderson, Kill & Olick, P.C.

(57) ABSTRACT

A bovine- or human-derived calcium-binding protein with a prescribed amino acid sequence, a method for its production, and antibodies against the protein and uses thereof.

2 Claims, 9 Drawing Sheets

Fig.1

```
          10         20         30         40         50
           *          *          *          *          *
-CTGGCATTC CACACTTCTG TGCAGAGGGG TGAACGTAGT TTGGTAAA ATG ACT AAG  N
                                                     Met Thr Lys 60         70         80         90        100
  *          *          *          *          *
CTG GAA GAT CAC CTG GAG GGA ATC ATC AAC ATC TTC CAC CAG TAC TCC  N
Leu Glu Asp His Leu Glu Gly Ile Ile Asn Ile Phe His Gln Tyr Ser 110        120        130        140        150
  *          *          *          *          *
GTT CGG GTG GGG CAT TTC GAC ACC CTC AAC AAG CGT GAG CTG AAG CAG  N
Val Arg Val Gly His Phe Asp Thr Leu Asn Lys Arg Glu Leu Lys Gln 160        170        180        190        200
  *          *          *          *          *          N
CTG ATC ACA AAG GAA CTT CCC AAA ACC CTC CAG AAC ACC AAA GAT CAA  V8-P
Leu Ile Thr Lys Glu Leu Pro Lys Thr Leu Gln Asn Thr Lys Asp Gln  ---
```

Fig. 2

```
         210       220       230       240
       *   *    *   *    *   *    *   *
CCT ACC ATT GAC AAA ATA TTC CAA GAC CTG GAT GCC GAT AAA GAC GGA
Pro Thr Ile Asp Lys Ile Phe Gln Asp Leu Asp Ala Asp Lys Asp Gly
                                                              N V8-P
                                                                Lysyl-P
    250       260       270       280       290
  *   *    *   *    *   *    *   *    *   *
GCC GTC AGC TTT GAG GAA TTC GTA GTC CTG GTG TCC AGG GTG CTG AAA
Ala Val Ser Phe Glu Glu Phe Val Val Leu Val Ser Arg Val Leu Lys
                                                              V8-P
                                                              Lysyl-P
300       310       320       330       340       350
  *    *   *    *   *    *   *    *   *    *   *
ACA GCC CAC ATA GAT ATC CAC AAA GAG TAGGAA GCTCTTTCCA GCAATGTCCC
Thr Ala His Ile Asp Ile His Lys Glu
                                                              V8-P
                                                              Lysyl-P
   360       370       380       390       400       410
 *   *    *   *    *   *    *   *    *   *    *   *
CAAGAAGACT TACCCTTCTC CTCCCTGAGG CTGCCTTACC CGAGGGAAGA GAGAATTAAT 420       430
 *   *    *
AAACGTACTT TGGCAAAGTT
```

CALCIUM-BINDING PROTEINS

This is a divisional of U.S. Ser. No. 568,310 filed Dec. 6, 1995, now U.S. Pat. No. 5,976,832.

BACKGROUND OF INVENTION

1. Field of the Invention

The present invention relates to novel calcium-binding proteins, DNA encoding them, antibodies against the calcium-binding proteins, hybridomas producing the antibodies, diagnostic agents comprising the antibodies, etc.

2. Related Art

Extracellular calcium ion concentration is known to play a role in the regulation of cellular proliferation and differentiation. On the other hand, intracellular calcium ion is one of the key transfer factors for intracellular signal transduction. The calcium signals are transduced by various calcium-binding proteins (CaBP). Calcium-binding proteins are largely classified as those with the EF-hand motif, such as calmodulin, troponin C, the S100 protein family, etc. and those without EF-hands, such as the anexine family. These are presumed to carry out separate and important physiological roles, but their physiological roles have not been completely elucidated.

Calmodulin mediates many calcium ion-dependent cellular reactions, and it is understood to be a ubiquitus CaBP required during mitosis. In contrast, CaBPs of the S100 protein family are expressed specifically according to cell cycle or cell type, and they are implicated in specific signal transduction for cellular division and differentiation. The S100 protein family includes S100α, S100β, calcyclin, MRP8, MRP14, etc., each of which have 2 EF-hand motifs.

Thus, the study of the presence and function of CaBPs is crucial for understanding the mechanisms of cell proliferation and differentiation, and is expected to yield useful knowledge for the understanding, diagnosis and treatment of the related diseases.

SUMMARY OF INVENTION

The present invention, therefore, provides novel calcium-binding proteins, as well as methods for their production, gene systems for their production, antibodies against the proteins, and methods for use thereof.

The present inventors have searched for calcium-binding proteins from among various specimens, and have found that a protein with considerable calcium-binding activity is present in bovine amniotic fluid. In addition, the inventors have isolated the calcium-binding protein to obtain a substantially pure protein, and have determined its full amino acid sequence and the sequence of the DNA encoding it. This calcium-binding protein is a hitherto-unknown novel protein belonging to the S100 protein family and present in extracellular fluid, and it has been named CAAF1 (Calcium binding protein in Amniotic Fluid 1).

In addition the present inventors succeeded to clone a novel cDNA by screening a human cDNA library using as a probe the above-mentioned bovine cDNA. In addition, the present inventors determined a nucleotide sequence of the human cDNA and a deduced amino acid sequence of human calcium-binding protein. This human calcium-binding is novel as well.

Furthermore, the present inventors have prepared antibodies against CAAF1, have studied the presence of the proteins in various tissues, and have also constructed a system for a quantitative assay thereof and have found their usefulness as diagnostic agents for a number of diseases.

Thus, the present invention provides calcium-binding proteins which may comprise any amino acid sequence which is substantially identical to the amino acid sequence shown in SEQ ID NO: 1 or 12.

The present invention further provides DNAs encoding the above-mentioned proteins, expression vectors including the DNA, and host cells transformed with the expression vectors.

The present invention still further provides a method for producing the calcium-binding proteins by extraction from bovine amniotic fluid or tissue, human tissue, or by using the above-mentioned host cells.

The present invention still further provides antibodies against the calcium-binding proteins, hybridomas which produce the antibodies, and methods of producing the antibodies.

The present invention still further provides diagnostic agents comprising the antibodies and analysis methods employing them.

BRIEF EXPLANATION OF THE DRAWINGS

FIG. 1 shows the amino acid sequence of bovine calcium-binding protein and the DNA sequence encoding it. In FIG. 1, the lines labelled as N indicate the results of determining the N-terminal amino acid sequence of the protein, and the dotted lines labelled as V8-P indicate the amino acid sequence of the two peptide fragments produced when the protein was cut with S. aureus V8 proteinase.

FIG. 2 shows the amino acid sequence of bovine calcium-binding protein and the DNA sequence encoding it. In FIG. 2, the lines labelled as N indicate the results of determining the N-terminal amino acid sequence of the protein, the dotted lines labelled as V8-P indicate the amino acid sequence of the two peptide fragments produced when the protein was cut with S. aureus V8 proteinase, and broken lines labelled as Lysyl-P indicate the amino acid sequence of fragments produced when the protein was cut with lysylendopeptidase.

In FIG. 3, lane 1 represents electrophoresis in the presence of mercaptoethanol and lane 2 in the absence thereof.

In FIG. 4, CAAF1 is contained in the portions denoted by *1.

DETAILED DESCRIPTION OF THE INVENTION

Figure 3:
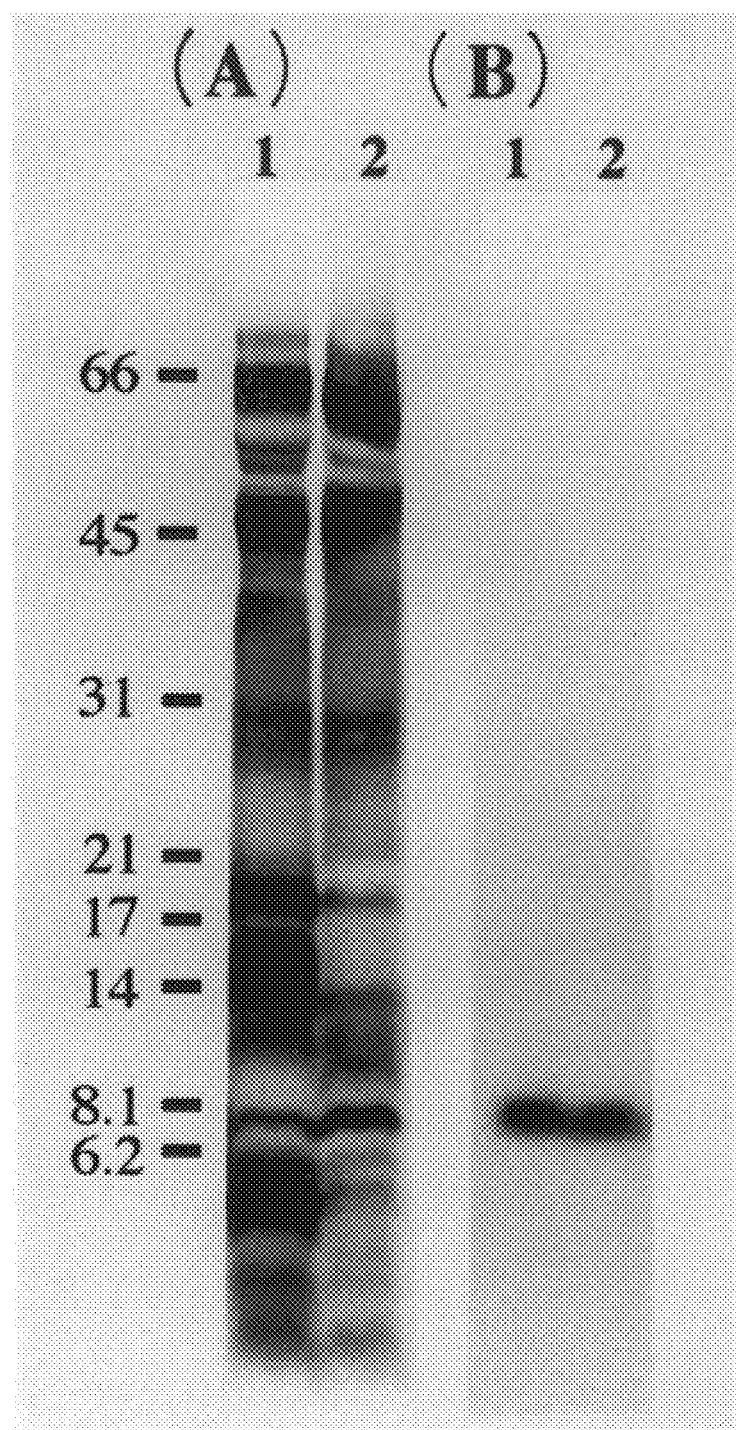
FIG. 3 shows electrophoretic patterns of bovine amniotic fluid with a Tricine-SDS-PAGE silver staining gel (A) and $^{45}Ca^{2+}$ overlay autoradiogram after Tricine-SDS-PAGE (B).

The calcium-binding protein of the present invention comprises any amino acid sequence which is substantially identical to the amino acid sequence listed in SEQ ID NO: 19 or 20. By "substantially identical" is meant that it is either exactly identical or is modified at one or a few amino acids while retaining the calcium-binding activity. "Modified" as used here refers to a change in the amino acid sequence listed in SEQ ID NO: 1 or 12 by a deletion, addition or amino acid substitution, or a combination thereof.

Furthermore, "a few" means less than, for example, about 10% of the entire number of amino acids of the amino acid sequence listed in SEQ ID NO: 19 or 20, such as 10 or fewer, and preferable 5 or fewer. Thus, according to the present invention, any amino acid sequence which is substantially identical to the amino acid sequence listed in SEQ ID NO: 19 or 20 encompasses amino acid sequences with an addition, deletion or substitution of 1 to 10, and preferably 1 to 5 amino acids which still have calcium-binding activity.

The present invention also includes fragments of the calcium-binding proteins having the various amino acid sequences described above. Such fragments are useful as immunogens for producing antibodies against the calcium-binding protein, regardless of whether or not they have calcium-binding activity.

The present invention also encompasses fused proteins of the above-mentioned calcium-binding protein or fragments thereof and other protein. The partner protein composing the fused protein may be any desired protein including glutathione-S-transferase, superoxide dismutase, lacZ or the like. Such fused proteins are useful for efficient expression of the calcium-binding protein of the present invention or fragments thereof by recombinant methods.

The present invention also relates to derivatives of the above-mentioned calcium-binding proteins and fragments thereof.

Derivatives of the calcium-binding protein within the scope of the present specification include glycosylated variants and covalent and aggregated conjugates with other chemical components. Covalent derivatives may be prepared by bonding with a functional group on an amino acid side chain or the N- or C-terminal of the calcium-binding protein, by a method well-known to those skilled in the art. Such derivatives include fatty esters and amides of carboxyl terminal or carboxyl group-containing residues, O-acyl derivatives of residues containing a hydroxyl group, and N-acyl derivatives of amino terminal or amino group-containing residues such as lysine or arginine, but are not limited to these. The alkyl component of the acyl group may be selected from, for example straight chain alkyl groups of $C_3$–$C_{18}$ to form alkanoyl aroyls.

The major derivatives are covalent conjugates of other proteins with a calcium-binding protein such as CAAF1 or fragments thereof. These derivatives are obtained either by recombinant culturing or by synthesis using substances known by those skilled in the art to be useful for N- or C-terminal fusion or for crosslinking of proteins through reactive side groups. Preferred reaction sites between a crosslinking agent and a calcium-binding protein such as CAAF1 are free amino groups, free carboxyl groups, carbohydrates and cysteine residues.

The present invention also relates to uses of the derivative resulting from covalent or aggregate association with a chemical component. The calcium-binding protein of the present invention may also be radioiodinated by, for example, the chloramine T method, or conjugated to a fluorescent component such as a rare earth metal chelate or other types of detectable group, to be labelled for use in, for example, an assay system for the calcium-binding protein.

The present invention further provides a method for producing the above-mentioned calcium-binding protein, fragments thereof, or fused proteins thereof.

The calcium-binding protein having the amino acid sequence listed as Sequence No. 1 or 12 may be isolated or purified from, for example, bovine amniotic fluid or other tissue, or human tissues. The isolation or purification may be performed by combining any of a variety of known purification methods, to the required degree of purity. Methods of purification which may be used include cationic exchange, anionic exchange, gel filtration, hydrophobic, isoelectric, immunologic affinity, chelate affinity, reverse phase and other kinds of chromatography, as well as fractional precipitation, etc. Other methods may also be used.

After obtaining the calcium-binding protein in sufficient purity and amount, its amino acid sequence from the N-terminal may be determined using a protein sequencer. The amino acid sequence outside the vicinity of the N-terminal may be determined, for example, by first decomposing the calcium-binding protein with a suitable protease or the like, purifying the fragment peptides obtained by the decomposition using a purification method such as reverse phase chromatography, determining the amino acid sequence from the N-terminals in the same manner, and then combining the sequences to determine the entire amino acid sequence.

The entire amino acid sequence may be determined in this manner, but such a method is not always necessary. For example, the general method described below may be used to clone DNA encoding the calcium-binding protein from part of the amino acid sequence, determine its nucleotide sequence, and deduce the amino acid sequence of the calcium-binding protein from the cDNA sequence.

The calcium-binding proteins of the present invention and fragments thereof may also be chemically synthesized by conventional methods. Such methods include those described in Janis D. Young, Solid Phase Peptide Synthesis, (Pierce Chemical Co., Rockford, Ill., 1984); M. Bondanszky and A. Bondanszky, The Practice of Peptide Synthesis, (Springer-Verlag, N.Y., 1984); and M. Bondanszky, The Principles of Peptide Synthesis, (Springer-Verlag, N.Y., 1984).

These are all included in the present specification as reference. For example, the azide method, acid chloride method, acid anhydride method, mixed acid anhydride method, active ester (e.g. p-nitrophenyl ester, N-hydroxy succinimide ester or cyanomethyl ester) method, carbodiimidazole method, oxidation-reduction method or DCC/additive method may be used. Both solid phase and liquid phase synthesis may be applied in the aforementioned methods.

The calcium-binding proteins of the present invention may be appropriately prepared according to the methods mentioned above which are typically used for peptide synthesis, and this usually involves the so-called step technique involving condensation of amino acids in order one-by-one onto the terminal amino acid, or coupling of peptide fragments onto the terminal amino acid. In order to avoid coupling at wrong sites, the amino groups not used in the coupling reaction must be protected.

When solid phase synthesis is employed, the C-terminal amino acid is bound to an insoluble carrier or support through its carboxyl group. The insoluble carrier is not particularly restricted so long as it is attachable to the reactive carboxyl group. Examples of insoluble carriers of this type include halomethyl resins, such as chloromethyl and bromomethyl resins, hydroxymethyl resins, phenol resins, tert-alkyloxycarbonyl hydrazide resins, and the like.

The amino acids whose amino groups have been protected are successively linked by condensation between their activated carboxyl groups and the reactive amino group of the already formed peptide chain, for a stepwise synthesis of the peptide. Once the complete sequence has been synthesized, the peptide is cut off from the insoluble carrier to obtain the peptide. This solid phase approach is described in general terms by Merrifield, et al. in J. Am. Chem. Soc., 85: 2149–2156 (1963). This explanation is incorporated into the present specification for reference.

A common means of peptide separation, for example extraction, precipitation, electrophoresis or a chromatography technique, may be used to isolate and purify the prepared calcium-binding protein or fragments thereof from the reaction mixture.

The calcium-binding protein of the present invention or fragments or fused proteins thereof may also be produced by a genetic engineering method. In such methods, host cells transformed by an expression vector comprising DNA encoding the desired protein or polypeptide are cultured and the protein or polypeptide of interest is collected from the culture. The host cells for this purpose may be either prokaryotic or eukaryotic cells. The prokaryotic cells may be, for example, bacteria which may be either gram-positive or gram-negative bacteria.

An example of a gram-negative bacterium is *Escherichia coli*, and examples of gram-positive bacteria are *Bacillus subtilis, Bacillus liqueformis*, etc., and commonly used hosts may be used appropriately. Other prokaryotic host cells which may be used include microorganisms of the genus Actinomyces and the genus Streptomyces.

The eukaryotic host may be either a lower eukaryotic host or higher eukaryotic host. Examples of lower eukaryotic hosts include gemella, fungi, etc. Preferred fungi are unicellular fungi such as yeast, or filamentous fungi. The yeast may be yeast of the genus Saccharomyces, such as *Saccharomyces cerevisiae*, and the filamentous fungi may be filamentous fungi of the genus Aspergillus, such as *Aspergillus niger* and *Aspergillus orizae*, as well as filamentous fungi of the genus Penicillus.

The higher eukaryotic organism host may be either an animal or plant. Animal hosts include insects and their cultured cells, mammals and their cultured cells, etc. Typical insects used are silk worm and cultured cells thereof, and mammals used are mice, rats, hamsters, cows, pigs, etc. and cultured cells thereof, as well as cultured human cells. Specific examples of animal cells include Chinese hamster ovary cells (CHO), HeLa cells, baby rat kidney cells (BRK), simian cells (COS), etc.

When the host used is cells they are cultured, and when the host is an animal or plant it is raised or cultivated. The culturing, raising or cultivation may be conducted according to well-established conventional methods. A common method used for protein purification may be used to purify the protein of the present invention from cultures, and any of the purification methods, for example listed earlier for purification from, bovine amniotic fluid, may be appropriately combined.

The calcium-binding protein of the present invention or fragments thereof may be obtained at various degrees of purity, depending on the desired use. The purification may be achieved using the protein-refining technique disclosed in this specification, or by immunologic affinity chromatography with an antibody described in this specification. A summary of immunologic affinity chromatography is given in the present specification.

The present invention provides a gene, typically DNA, encoding the protein of the present invention, for production of the protein. This DNA typically has the nucleotide sequence listed in SEQ ID NO: 1 or 12, but it is not limited thereto, and DNA having various nucleotide sequences with degeneration of the codons coding for the amino acid sequence listed in SEQ ID NO: 1 or 12 are also included in the present invention. Furthermore, the above description implies that DNA encoding proteins which comprise amino acid sequences which are substantially identical to the amino acid sequence listed in SEQ ID NO: 1 or 12 are also included in the present invention. DNA encoding protein fragments or fused proteins of the above-mentioned protein is also included in the present invention.

The present invention also encompasses DNA which is sufficiently homologous with the different DNA described above so as to allow it to hybridize therewith, and which encodes a protein with calcium-binding activity. Factors influencing hybridization (or reassociation by which double strands of complementary DNA strands are formed) include temperature, salt concentration, base pair matching errors, length of DNA fragments, diversity, etc. The stability of associated double stranded nucleic acids is expressed in terms of melting temperature (Tm, temperature at which 50% melting occurs), and when the probe DNA is at least 150 base pairs long, hybridization is usually performed at the Tm −25° C. at which the highest hybridization rate may be achieved.

The Tm is affected by the homology between the nucleotide sequences of the probe and the DNA, but hybridization is commonly performed at a temperature of 68° C., or 42° C. in the presence of 50% formaldehyde. The conditions employed for such hybridization are, for example, 6×SSC, 50% formaldehyde, 5×Denhardt solution, 20 mM Tris-HCl, 0.5% SDS, 100 µg/ml denatured salmon sperm DNA, in pH 7.5 solution, 42° C., 24 hours. The degree of homology is preferably above 60%, and more preferably above 70%.

To obtain the DNA, typically, a cDNA library prepared from bovine or human tissue, such as fetal calf esophagus, human neutrophil, is screened using a probe designed from a partial amino acid sequence of the bovine or human calcium-binding protein of interest. The DNA obtained in this manner will have, for example, the nucleotide sequence listed in SEQ ID NO: 1 or 12. In this case, the amino acid sequence obtained from the purified calcium-binding protein may be used according to known techniques to isolate DNA encoding the calcium-binding protein and determine its nucleotide sequence.

For example, an amino acid sequence obtained from the calcium-binding protein may be used to devise a PCR primer and synthesize a DNA probe by RT-PCR, and then the DNA probe may be used to isolate the cDNA of the calcium-binding protein. A number of standard methods are either described or referred to in Maniatis, et al., Molecular Cloning, A Laboratory Manual (Cold Spring Harbor Laboratory, Cold Spring Harbor N.Y.) or F. M. Ausubel, et al., Biology (Greene Publishing Associates, Brooklyn, N.Y.).

Once the cDNA has been isolated, its nucleotide sequence may be determined by known techniques. From this nucleotide sequence, the amino acid sequence of CAAF1 which is the primary translation product, i.e. the amino acid sequence before possible posttranslational modification, may be deduced.

DNA encoding amino acid sequences which are not identical to but are substantially identical to the amino acid sequence listed in SEQ ID NO: 1 or 12, such as amino acid sequences modified by one or a few amino acid additions, deletions or substitutions, may be prepared, for example, using DNA with the nucleotide sequence listed in SEQ ID NO: 1 or 12 as a template, and inducing a site-specific mutation with a mutagenic primer.

The mutation site may be decided in advance, but that is not an essential condition. For example, in order to optimize the property of a mutant at a specific residue site, a random mutation may be induced at a target codon, and the subsequently expressed CAAF1 mutants screened for the desired property. There are methods publicly known to those skilled in the art for creating substitution mutations at predetermined sites of DNA with known sequences, and one of these is M13 primer mutation induction.

DNA encoding fragments of the above-mentioned protein may be prepared by cutting DNA encoding the protein longer than the fragment of interest with restriction endonuclease, or by shortening the DNA to a desired length with exonuclease, or by introducing a translation initiation codon or translation termination codon into DNA encoding the protein longer than the fragment of interest.

Alternatively, the DNA of the present invention may be chemically synthesized by common methods, for example solid phase synthesis, such as the phosphoamide method, etc.

DNA encoding a fused protein may be created by linking DNA encoding the calcium-binding protein of the present invention or a fragment thereof, with DNA encoding the partner protein which is to compose the fused protein.

For the purpose of the present invention, when the DNA sequences are functionally interrelated, they are functionally linked. For example, if the polypeptide is to be expressed as a precursor protein or is connected with localization of the polypeptide in the membrane or secretion of the polypeptide, the precursor sequence or secretion leader DNA is functionally linked to that of the polypeptide. To regulate transcription of the polypeptide, a promoter is functionally linked to the coding sequence. When the coding sequence is to be placed to allow translation, the ribosome-binding site is functionally linked to the coding sequence. In general, "functionally linked" means linked and within the reading frame. However, genetic factors such as a repressor genes are not adjacently linked but are linked to the operator sequence which regulates expression.

The present invention provides vectors which express DNA encoding the calcium-binding protein or a fragment thereof.

Expression vectors are usually selfreplicating DNA or RNA frames containing a gene of interest functionally linked to an appropriate gene regulating factor which is recognized in appropriate host cells. Such regulating factors are capable of acting on expression in appropriate hosts. The specific type of regulating factor required for expression depends on the final host cells used.

Gene regulating factors are generally prokaryotic promoter systems and eukaryotic promoter expression regulating systems, and they may be transcription promoters, any desired operator which regulates initiation of transcription, transcription enhancers which raise the level of mRNA expression, sequences coding for appropriate ribosome binding sites, and sequences which terminate transcription or translation. Expression vectors usually include replication origins from which the vectors replicate independently of host cells.

The vector of the present invention includes DNA encoding the protein of the present invention. This DNA may be under the regulation of a viral promoter, and it may encode a selective marker. The present invention also encompasses the use of expression vectors capable of expressing DNA encoding the protein of the present invention in prokaryotic or eukaryotic hosts. The vector is one which is compatible with the host, and the DNA encoding the protein of the present invention is inserted into the vector to allow its expression in the host containing the vector.

Expression vectors are generally designed for stable expression in their host cells, or for maximum amplification of the number of copies of the desired gene per cell. However, constant propagation of the expression vector in the host cell is not necessarily required. A vector containing no replication origin recognized by the host cell may be used for temporary expression of the protein of the invention in a variety of host cells. There may also be used vectors which incorporate DNA encoding the protein of the invention into the DNA of the host by recombination.

Such vectors include plasmids, viruses, bacteriophages, DNA fragments capable of being incorporated, and other vehicles capable of incorporating the DNA into the genome of the host. An expression vector is a specialized vector containing a genetic regulatory sequence which expresses a functionally linked gene. Plasmids are the most widely used form of vector, but vectors in various other forms which provide the same function and are known or will be known to those skilled in the art may also be suitably used according to the present specification.

Suitable hosts are, as mentioned above, prokaryotic organisms, lower eukaryotic organisms and yeast, and higher eukaryotic organisms. Prokaryotic organisms include gram-negative and gram-positive organisms, such as *E. coli* and *B. subtilis*. Lower eukaryotic organisms include yeasts such as *S. cerevisiae* and species of Pichia and Dictyostelium. Higher eukaryotic organisms include cultured tissue cell systems established from animals cells from both non-mammalian sources, such as insect cells and mammalian sources such as humans, primates and rodents.

Prokaryotic host-vector systems include a wide range of vectors for many diverse species. The terms "*E. coli*" and "its vector" in the present specification will be used in an inclusive sense to encompass equivalent vectors for other prokaryotic organisms. A representative vector for amplifying DNA is pBR322 or any desired derivative thereof. Vectors used to express the calcium-binding proteins or fragments thereof include, but are not limited to, those comprising lac promoter (pUC series), those comprising trp promoter (pBR322-trp), those comprising Ipp promoter (pIN series), those comprising γ-pP or pR promoter (pOTS) and those comprising the ptac hybrid promoter (pDR540).

For reference, see Brosius, et al., "Expression Vector Employing Lambda-, trp-, lac-, and Ipp-derived Promoters", Vectors: A Survey of Molecular Cloning Vectors and Their Uses (ed. by Raymond L. Rodriguez and David T. Denhardt), Buttersworth, Boston, 1988, Chap. 10, 205–236.

Lower eukaryotic organisms such as yeast and Dictyostelium may be transformed using a vector containing a sequence encoding the protein of the present invention. Many other strains and species may be used for the purpose of the present invention, but the most widely used lower eukaryotic host is the baker's yeast *Saccharomyces cerevisiae*, which will be used to comprehensively represent lower eukaryotic organisms. The yeast vector comprises a replication origin (provided it is not an incorporating type), a selection gene, a promoter, DNA encoding the protein of the invention, and sequences for translation termination, polyadenylation and transcription termination.

Suitable yeast expression vectors include constitutive promoters such as 3-phosphoglycerate kinase and various other glycolytic enzyme gene promoters or inductive promoters such as alcohol dehydrogenase 2 promoter or metallothionein promoter. Suitable vectors also include the following types of derivatives: autoreplicating low-copy types (e.g. YRp series), incorporating types (e.g. YIp series) and minichromosome types (e.g. YCp series).

Cultured tissue cells of higher eukaryotic organisms are the preferred type of host cells for expression of the functionally active calcium-binding protein. Theoretically, any system of cultured eukaryotic tissue cells may be used even if the source is an invertebrate animal. Mammalian cells, however, are preferred. The transformation or transfection and growth of such cells are carried out by routine techniques. Examples of useful cell systems are HeLa cells, Chinese hamster ovary (CHO) cell systems, baby rat kidney (BRK) cell systems, insect cell systems, and simian (COS) cell systems.

Expression vectors for such types of cell systems usually comprise a replication origin, a promoter, a ribosome-binding site, an RNA-splicing site (when genomic DNA is used), a polyadenylation site and a transcription termination site. These vectors usually also include a selection gene or amplification gene. Suitable expression vectors include plasmids, viruses and retroviruses carrying promoters derived from sources such as adenovirus, SV40, parvovirus, vaccinia virus and cytomegalovirus. Representative of such suitable expression vectors are pcDNA1, pCD (Okayama, et al., Mol. Cell Biol. 5: 1136–1142, 1985), pMC1neo Poly A (Thomas, et al., Cell 51: 503–512, 1987) and baculovirus vectors such as pAC373 and pAC610.

The present invention also provides cells transformed by a vector containing DNA encoding the calcium-binding protein or fragments thereof.

The transformed cells are cells which have been transformed or transfected with an expression vector for the calcium-binding protein prepared using a recombinant DNA technique. The transformed host cells express the calcium-binding protein or fragment thereof, but if the purpose is cloning, amplification or manipulation of the DNA, expression of the calcium-binding protein is not necessary.

The protein of the invention and DNA encoding it have a variety of uses. That is, the DNA may be used for production of the protein it encodes, and it is also particularly useful for detection and identification of genes coding for related or homologous calcium-binding proteins, genes coding for subtypes of the calcium-binding protein, and genes coding for the calcium-binding proteins of different species.

The present invention further relates to uses of the calcium-binding protein, fragments and peptides thereof, and fusion products of these, in various assay systems and diagnostic agents for detecting the presence of and quantifying the calcium-binding protein.

The calcium-binding proteins of the invention and fragments thereof may also be employed as standard substances in the above-mentioned assay systems.

The calcium-binding proteins of the invention and fragments thereof may also be used as immunogens for making antiserum or antibodies specific to the calcium-binding protein or fragments thereof. The purified calcium-binding protein may be used to screen monoclonal antibodies obtained by immunization with a low purity preparation of the calcium-binding protein. The calcium-binding protein may also be used as an immunogen for producing the antibody of the present invention.

The present invention further provides antibodies with affinity to the calcium-binding protein. The present invention relates to, for example, antibodies with affinity to or produced against the calcium-binding protein with the amino acid sequence listed as in SEQ ID NO: 1 or 12, and fragments of the antibody. The antibodies may be produced against either the native or the recombinant form of the calcium-binding protein.

Antibodies against a fragment of the calcium-binding protein of the invention may be produced by immunizing an animal with a conjugate of an immunogenic protein and the fragment. A monoclonal antibody may be prepared from cells secreting the desired antibodies. These antibodies may be screened by their binding with the calcium-binding protein.

The calcium-binding protein of the invention or fragment thereof may be fused or covalently conjugated to a polypeptide to be used as an immunogen for immunization. The calcium-binding protein or fragment thereof may also be fused or covalently conjugated to various common immunogens, for example, keyhole limpet hemocyanin, bovine serum albumin, tetanus toxoid, and the like, for immunization. The animal to be immunized may. be a cow, horse, goat, sheep, rabbit, chicken, guinea pig, rat, mouse, etc. and there are no restrictions provided the desired antibody can be obtained from the animal upon immunization.

For explanations regarding methods for preparing polyclonal antiserum, refer to, for example, Microbiology, Hoeber Medical Division (Harper and Row, 1969), Landsteiner, Specificity of Serological Reactions (Dover Publications, New York, 1962) and Williams, et al., Methods in Immunology and Immunochemistry, Vol. 1 (Academic Press, New York, 1967) (These are all incorporated in the present specification by reference). A typical method involves booster immunization of an animal with the antigen.

Polyclonal antibodies according to the present invention may be obtained according to a common method, by periodically immunizing an animal such as a horse, goat, sheep, rabbit, chicken or guinea pig with the above-mentioned antigen peptide either alone or mixed with an adjuvant.

Blood, eggs, etc. may be taken from the animal which has been immunized preferably 3 times or more, and the polyclonal antibodies recovered.

The present invention further provides monoclonal antibodies with binding affinity to the calcium-binding protein. The present invention still further provides hybridomas which produce the above-mentioned monoclonal antibodies.

In many cases, it is desirable for monoclonal antibodies to be prepared from a mammalian host, for example a rodent such as a mice or rat, a primate, human, etc. Explanations of a technique for preparing such monoclonal antibodies may be found in Stites, et al., Basic and Clinical Immunology, (Lang Medical Publications, Los Altos, Calif., 4th edition) and references therein, and particularly in Kohler and Milstein, Nature 256: 495–497 (1975) (discussing one method of producing monoclonal antibodies).

To briefly summarize, mice, rats, etc. are periodically immunized with the above-mentioned antigen either alone or in admixture with an adjuvant. Preferably after three or more immunizations, the spleen or lymph nodes are extracted and the B cells are fused with suitable myeloma cells. The fused cell lines are "hybridomas" which may be cultured in vitro. The resultant hybridoma cells are cultured in an appropriate culture solution such as HAT-RPMI1640 medium containing 10% fetal calf serum.

The antibodies produced in the culture supernatants are detected by, for example, RIA or ELISA, and the hybridoma cell lines producing antibodies which react specifically with the calcium-binding protein are selected and cloned. Each of the clones secretes one type of antibody against the immunogen. Each individual antibody type obtained is the product of a single B cell from the immunized animal, produced in response to a specific site (epitope) recognized on the immunogenic substance.

Monoclonal antibodies reacting with the calcium-binding protein of the invention may be recovered from ascites fluid obtained after transplanting hybridoma cells into the peritoneal of mice or rats, for example. They may also be recovered from a culture supernatant of the hybridoma cells.

The recovered monoclonal or polyclonal antibodies may be separated and purified by a publicly known method such as ammonium sulfate precipitation or chromatography.

The antibodies of the invention may be used for affinity chromatography. The affinity chromatography may be used to purify the calcium-binding protein of the invention. A column is prepared with an antibody bound to a solid carrier, such as particles of agarose, sepharose or a similar substance, a sample containing the calcium-binding protein is passed through the column, the column is washed, and then a weak denaturant is flowed through to elute out the purified calcium-binding protein.

The present invention further provides detection methods and assay methods for the calcium-binding protein and fragments thereof, which methods employ the above-mentioned antibodies.

The detection systems and assay systems for the calcium-binding protein may be either homogeneous (not including a stage of separating the free reagent and the calcium-binding protein-antibody complex) or heterogeneous (including the separating stage).

The detection system and assay system for the calcium-binding protein of the present invention typically comprises a labelled antibody with binding affinity to the calcium-binding protein, a source of the calcium-binding protein (native or recombinant) and means for separating the conjugate from the free labelled compound, for example a solid-phase antibody with binding affinity to the calcium-binding protein for immobilization of the calcium-binding protein.

In these assay systems, the antibody or the calcium-binding protein and fragments thereof may be directly or indirectly labelled by covalent or non-covalent bonding to obtain a direct or indirect detectable signal. Direct labelling methods include radioactive labelling, such as with $^{125}$I, enzymes (U.S. Pat. No. 3,645,090), e.g. peroxidase and alkaline phosphatase, and fluorescent labelling (U.S. Pat. No. 3,940,475). This also includes biotinylation and binding to biotin of avidin or streptoavidin labelled with one of the aforementioned labelling groups. An unlabelled antibody may be used by employing a labelled second antibody which recognizes that antibody.

Using an obtained antibody against the calcium-binding protein, and constructing a publicly known immunoassay system based on radioimmunoassay (RIA), enzyme immunoassay (EIA) or fluorescent immunoassay (FIA), it is possible to detect and measure the calcium-binding protein or fragments thereof.

One example of a known immunoassay method that may be applied is the so-called competitive immunoassay. For example, a prescribed amount of the calcium-binding protein which has been labelled with a radioactive isotope or the like is mixed with a specimen, and the anti-calcium-binding protein antibody is mixed therewith and allowed to react with the calcium-binding protein in the specimen and the labelled calcium-binding protein.

Since the calcium-binding protein in the specimen competes with the labelled calcium-binding protein to react with the anti-calcium-binding protein antibody, the reaction with the labelled calcium-binding protein decreases in proportion to the calcium-binding protein present in the specimen. After the reaction, the anti-calcium-binding protein antibody is either first bound to a solid-phase carrier, or anti-Ig antibody, protein A are reacted to the anti-calcium-binding protein antibody to separate the bound and unbound labelled calcium-binding protein. The non-binding fraction is removed by a commonly used method, and the bound radioactive isotope or other labelling is detected to allow measurement of the calcium-binding protein.

Another example of a publicly known immunoassay method which may be applied is the so-called double antibody sandwich system. For example, the anti-calcium-binding protein antibody is bound to a solid-phase carrier commonly employed in immunoassay methods, such as a microtiter plate, beads, nitrocellulose membrane, nylon membrane, etc. and it is contacted with a specimen to react the calcium-binding protein in the specimen with the anti-calcium-binding protein antibody on the solid-phase carrier. The non-binding fraction is washed out by a common method and the anti-calcium-binding protein antibody which has been labelled with a radioactive isotope, enzyme, fluorescent substance, biotin or the like, is contacted with the calcium-binding protein bound to the anti-calcium-binding protein antibody on the carrier for reaction therewith.

The non-binding fraction is washed out by a commonly used method, and the labelled radioactive isotope, enzyme, fluorescent substance or biotin is detected to allow measurement of the calcium-binding protein. The anti-calcium-binding protein antibody and labelled anti-calcium-binding protein antibody used in this assay system may be monoclonal antibodies, polyclonal antibodies or a combination thereof. What is essential here is proper combinations of antibodies to allow the carrier-bound antibody/calcium-binding protein complex to bind to the labelled antibody, and such antibody combinations may be selected to suit the construction of any of the above-mentioned systems.

The calcium-binding proteins or fragments thereof in tissue may also be detected by immunohistological staining, which also reveals the local morphology of tissues or cells. Examples of antibody labelling using immunohistological staining include fluorescent pigments and enzymes for light microscopy and ferritin and gold colloids for electron microscopy. The immunohistological staining is typically performed by, for example, fixing tissue slices or cells with an appropriate fixing agent such as alcohol, acetone, paraformaldehyde, etc. and reacting the anti-calcium-binding protein antibody therewith. After washing, detection of the labelling is made directly in the case of direct labelling, after further reaction with a labelled moiety and washing in the case of indirect labelling, by fluorescent microscope in the case of fluorescent labelling, by light microscope after reaction with a suitable substrate in the case of enzyme labelling, and by electron microscope in the case of metal particle labelling.

These immunoassay methods have been thoroughly discussed in literature.

An antibody of the present invention is also useful for diagnosis.

From the results obtained by the immunohistological staining and immunoassay described above, it is possible to determine the tissue and cellular distribution of the calcium-binding protein. This will yield information on the physiological role of the calcium-binding protein and elucidate its connection with various diseases. Its connection with diseases will provide clues for its utility as a diagnostic agent for those diseases.

For example, an antigen specifically present in cancerous cells may be useful as a marker for tumor diagnosis. Also, antigens abundantly present in cell groups involved in inflammation, such as neutrophils, leak out into the blood as inflammation progresses, and thus their blood concentrations may be useful as markers for diagnosis of inflammation. Furthermore, antigens which are abnormally expressed in connection with skin diseases may be used as markers for those diseases.

Thus, assay systems for the above-mentioned calcium-binding protein or fragments thereof may be used in diagnostic agents to yield useful information as an inflammatory disease marker, a neoplastic disease (especially epidermoid carcinoma of the skin, esophagus, respiratory tract, cervix, etc.) marker, a skin disease marker or a blood disease marker, for screening of patients during examinations, specifying the nature of diseases, monitoring the effects of treatment, etc.

Specimens to be assayed include patient blood, saliva and other body fluids, urine, feces and other excrement, extracted tissue, cells, and the like.

EXAMPLES

The present invention will now be explained in more concrete terms by way of the following examples.

Example 1

Detection of CAAF1

CAAF1 was detected by the following method. A sample was subjected to Tricine-SDS-PAGE according to the method described in Analytical Biochemistry 166, 368–379 (1987), in the presence and in the absence of 2-mercaptoethanol.

The gel was silver-stained with a Silver Stain Kit Wako (Wako Pure Chemical Industries) to detect the protein. Using amniotic fluid from cows in the 4th month of pregnancy as samples gave bands of many other proteins, as well as a band located at about 7 KDa corresponding to the CAAF1 calcium-binding protein in the bovine amniotic fluid (FIG. 3).

The calcium-binding protein was also detected by $^{45}$Ca overlay autoradiography as described below. The protein in the gel which had been subjected to Tricine-SDS-PAGE was transferred (by electroblotting) to an Immobilon-P (Millipore) membrane by the semidry method. The transfer membrane was shaken for 15 minutes in an overlay buffer (60 mM KCl, 5 mM $MgCl_2$, 10 mM imidazole-HCl, pH 6.8) three times, and then shaken at 37° C. for 30 minutes in an overlay buffer containing 3.7 MBq/l $^{45}Ca^{2+}$ to bind the $^{45}Ca^{2+}$. Washing for 10 minutes with the overlay buffer was repeated 3 times, and then after an additional 10 minutes of shaking in 50% ethanol, the transfer membrane was dried and autoradiography was performed. Amniotic fluid from cows in the 4th month of pregnancy gave a small number of other weak bands as well as a strong band of apparent molecular weight about 7 KDa corresponding to CAAF1 (FIG. 3). This confirmed the presence of a large amount of the calcium-binding protein in the bovine amniotic fluid.

Example 2

Purification of CAAF1

Figure 4:
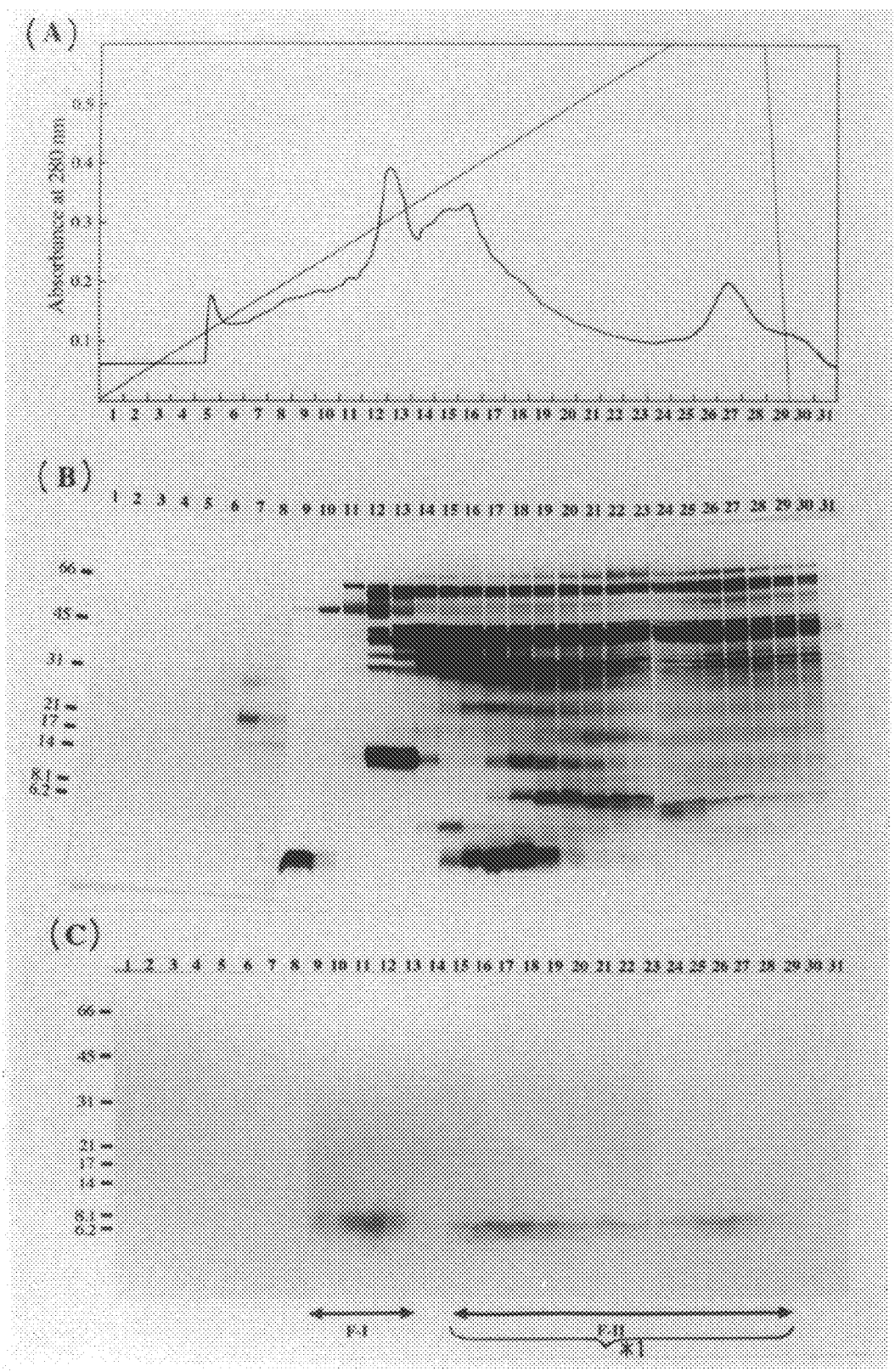
FIG. 4 shows electrophoretic patterns of bovine amniotic fluid with cationic exchange chromatography (A), each of the fractions thereof in a Tricine-SDS-PAGE silver staining gel (B) and with $^{45}Ca^{2+}$ overlay autoradiography after Tricine-SDS-PAGE (C).

Acetic acid was added to 3 liters of amniotic fluid from cows in the 4th month of pregnancy, to adjust the pH to 3.0. The resulting precipitate was removed by centrifugation for 40 minutes at 9000×G. and the supernatant was filtered and subjected to cation exchange chromatography. The supernatant was then applied to a S-Sepharose fast flow column (Pharmacia) equilibrated with 1 M acetic acid, and the adsorbed protein was eluted out with an ammonium acetate concentration gradient. When each of the fractions was subjected to $^{45}$Ca overlay autoradiography, CAAF1 was detected in a wide range of fractions from 0.5–1 M ammonium acetate (FIG. 4).

The CAAF1-containing fractions were collected, lyophilized, and reconstituted with 5 ml of 1 M acetic acid. The solution was gel filtrated by a 16/90 Sephadex-G75 fine column (Pharmacia) equilibrated with 1 M acetic acid. Each of the fractions was subjected to Tricine-SDS-PAGE followed by $^{45}Ca^{2+}$ overlay autoradiography in the same manner and the CAAF1-containing fractions were then subjected twice to reverse phase chromatography. That is, they were applied to a column filled with TSK ODS-120T (Toso) equilibrated with 0.1% trifluoroacetic acid, and the adsorbed protein was eluted out with an acetonitrile concentration gradient. CAAF1 was eluted out near ca. 40% acetonitrile concentration. The target fraction was then applied to a column filled with TSK Phenyl-5PW (Toso) equilibrated with 0.1% trifluoroacetic acid, and the adsorbed protein was eluted out with an acetonitrile concentration gradient. CAAF1 was eluted out near ca. 30% acetonitrile concentration.

Figure 5:
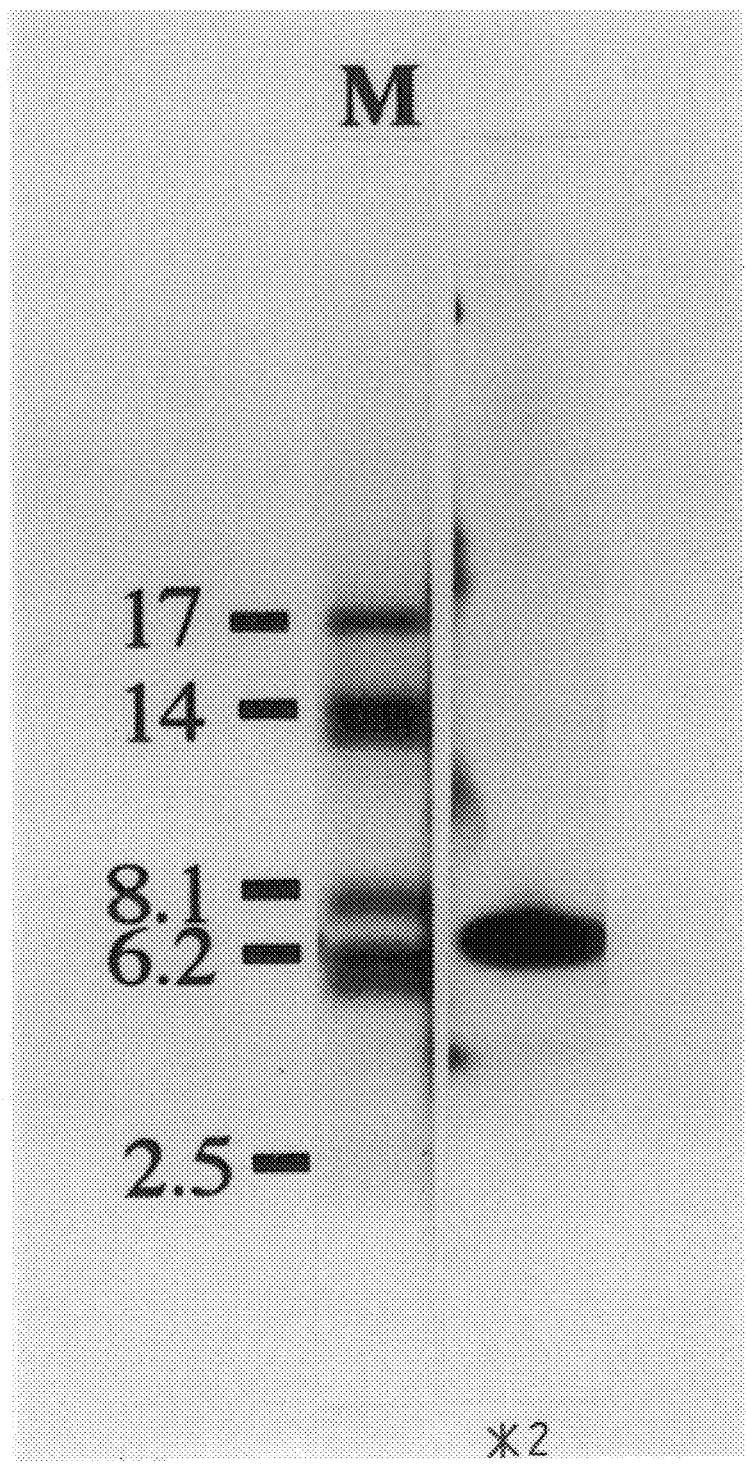
FIG. 5 shows an electrophoretic pattern of purified bovine CAAF1 in an SDS-PAGE-analyzed silver stained gel.

Through a series of purification procedures there was obtained 150 µg of the calcium-binding protein CAAF1 substantially unitary, producing a single band of apparent molecular weight about 7 KDa upon silver staining after Tricine-SDS-PAGE (FIG. 5).

Figure 6:
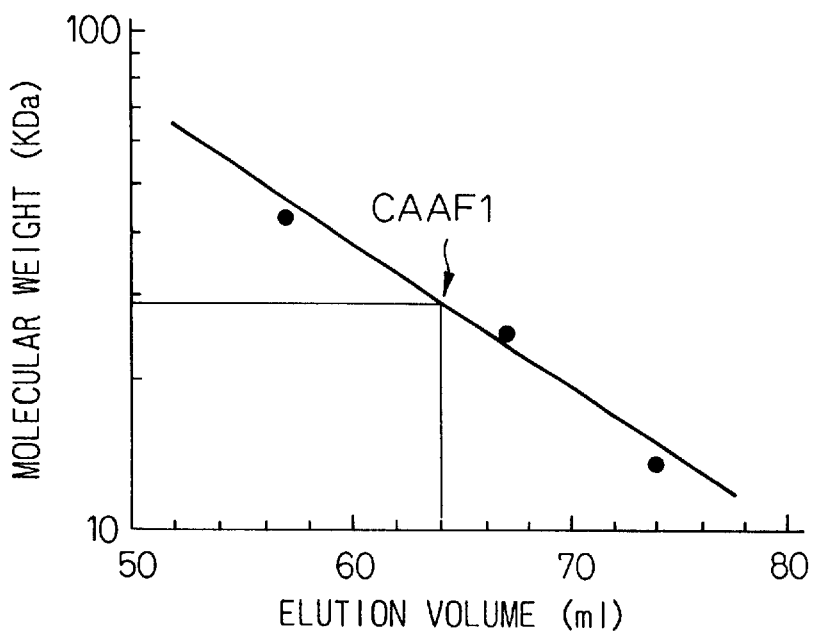
FIG. 6 is a graph showing the apparent molecular weight of bovine CAAF1 by gel filtration chromatography.
Figure 7:
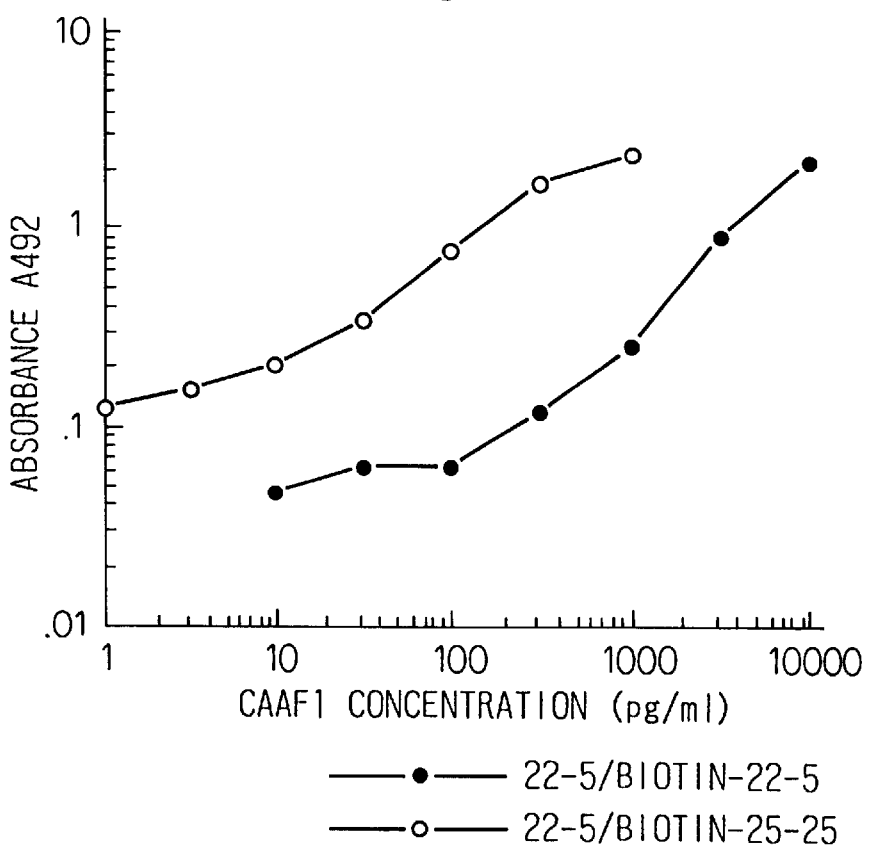
FIG. 7 is a graph showing an example of the relationship between the calcium-binding protein concentration and absorbance (calibration curve) when the calcium-binding protein is assayed using biotin-labelled anti-calcium-binding protein antibody.
Figure 8:
FIG. 8 is a photograph which shows the results of immunohistological staining and morphology of tissue slice of fetal calf skin (cuticle) using CAAF1-22-5 monoclonal antibody.
Figure 9:
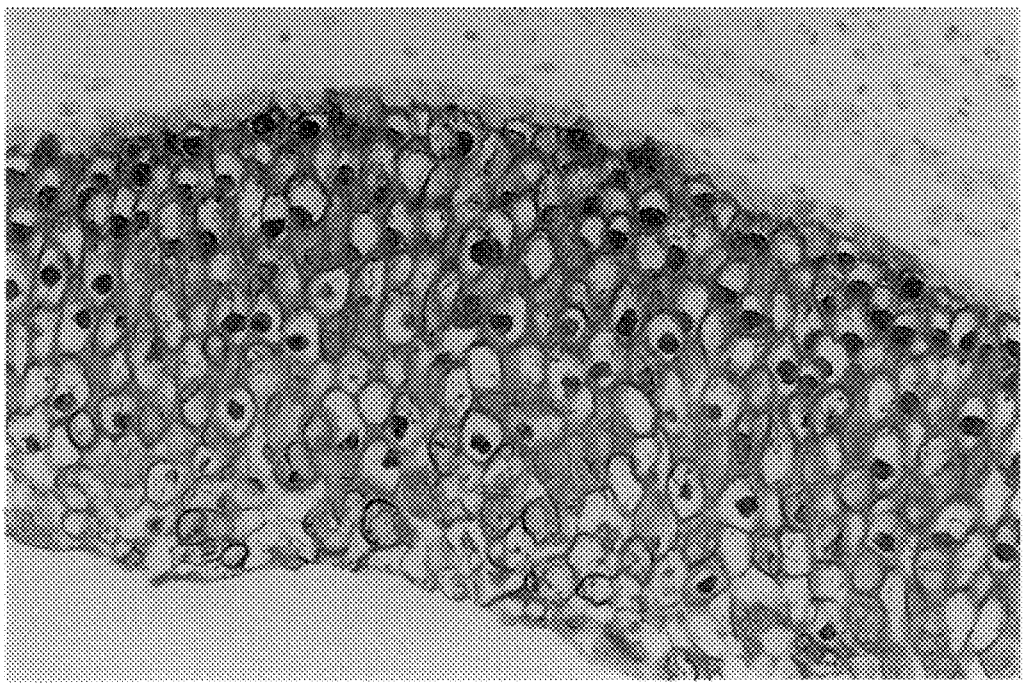
FIG. 9 is a photograph which shows the results of immunohistological staining and morphology of tissue slice of fetal calf espagus (mucosa) using CAAF1-22-5 monoclonal antibody.
Figure 10:
FIG. 10 is a photograph which shows the results of immunohistological staining and morphology of tissue slice of fetal calf amniotic membrane using CAAF1-22-5 monoclonal antibody.
Figure 11:
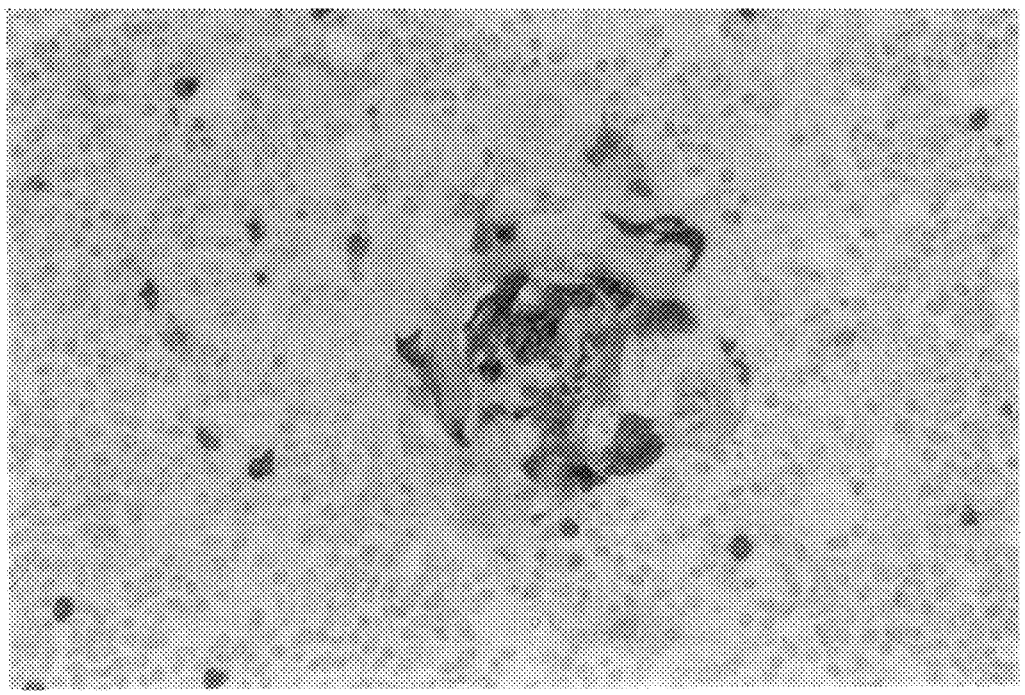
FIG. 11 is a photograph which shows the results of immunohistological staining and morphology of tissue slice of fetal calf thymus using CAAF1-22-5 monoclonal antibody.
Figure 12:
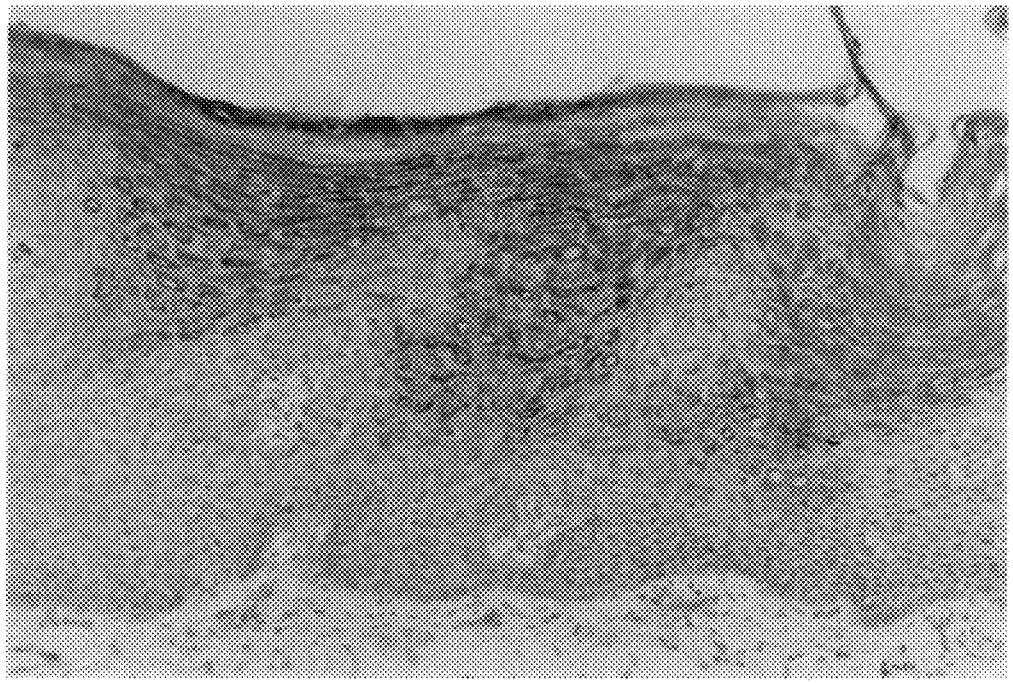
FIG. 12 is a photograph which shows the results of immunohistological staining and morphology of tissue slice of adult human esophagus (normal membrane) using CAAF1-22-5 monoclonal antibody.
Figure 13:
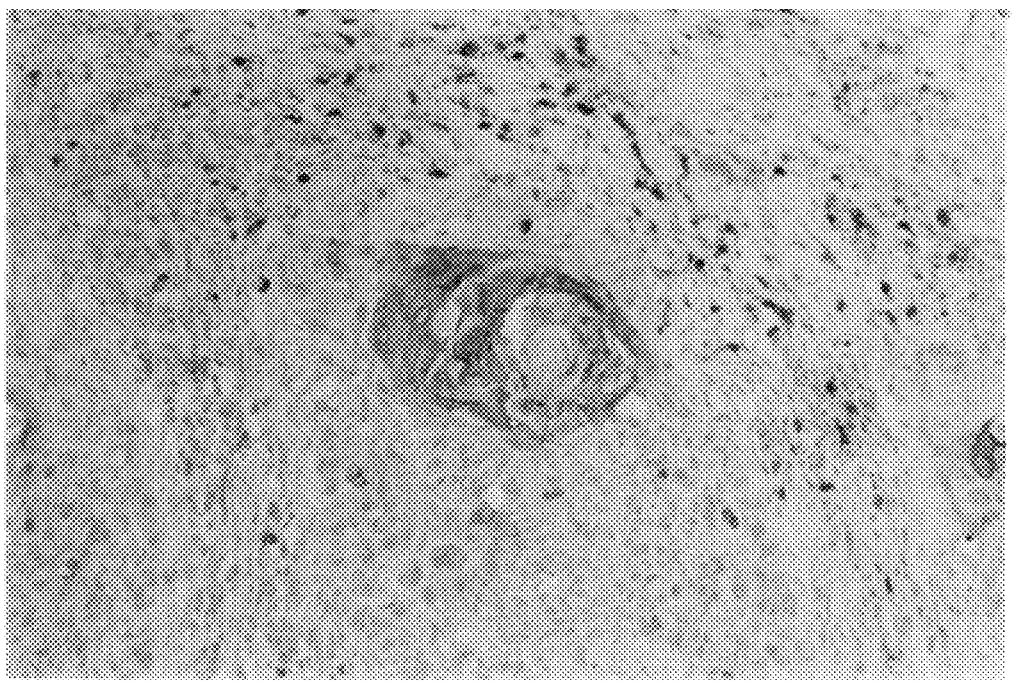
FIG. 13 is a photograph which shows the results of immunohistological staining and morphology of tissue slice of adult human esophagus (cancer cells and infiltrated cells) using CAAF1-22-5 monoclonal antibody.

Upon estimation of the molecular weight of the protein by gel filtration using 16/60 Superdex 75 pg (Pharmacia), CAAF1 exhibited an elution peak at about 30 KDa (FIG. 6). This suggests that CAAF1 exists in solution as homotrimers or tetramers.

Example 3

Determination of CAAF1 Amino Acid Sequence

The amino acid sequence of the purified CAAF1 was determined from the N-terminal to the 51st amino acid residue using a protein sequencer (Applied Biosystems, Model 1477A). The sequence was as follows:

(SEQ ID NO: 2)
Thr Lys Leu Glu Asp His Leu Glu Gly Ile Ile Asn Ile

Phe His Gln Tyr Ser Val Arg Val Gly His Phe Asp Thr

Leu Asn Lys Arg Glu Leu Lys Gln Leu Ile Thr Lys Glu

Leu Pro Lys Thr Leu Gln Asn Thr Lys Asp Gln Pro

A 5 μg portion of the CAAF1 was digested at 37° C. overnight with lysylendopeptidase (EC 3.4.21.50, Wako Pure Chemical Industries ) or *S. aureus* V8 proteinase (endoproteinase Glu-C, EC 3.4.21.19, Boehringer Mannheim), and the respective decomposition products (L1, L2, L3 and V1, V2) were purified by reverse phase chromatography. The amino acid sequences were determined with a protein sequencer. The sequences of each of the fragments obtained with lysylendopeptidase were as follows:

L1: Ile Phe Gln Asp Leu Asp Ala Asp            (SEQ ID NO: 3)

L2: Asp Gly Ala Val Ser Phe Glu Glu Phe Val Val Leu (SEQ ID NO: 4)

L3: Thr Ala His Ile Asp Ile His Lys Glu        (SEQ ID NO: 5)

The sequences of each of the fragments obtained with V8 proteinase were as follows:

V1: Leu Pro Lys Thr Leu Gln Asn Thr Lys Asp Gln Pro Thr   (SEQ ID NO: 6)
    Ile Asp Lys Ile Phe Gln Asp Leu Asp Ala Asp Lys Asp
    Gly Ala Val Ser Phe

V2: Glu Phe Val Val Leu Val Ser Arg Val Leu Lys Thr Ala   (SEQ ID NO: 7)
    His Ile Asp Ile His Lys Glu

The entire amino acid sequence of CAAF1 was determined by comparing and joining the N-terminal and partial peptide amino acid sequences (FIGS. 1 and 2, underlined portion). This sequence comprises the amino acid sequence listed as Sequence No.1 (FIGS. 1 and 2) without the N-terminal methionine.

Example 4

Preparation of cDNA Library from Fetal Calf Esophageal Tissue

RNA was extracted from 2.5 g of fetal calf esophageal tissue by the AGPC method, to obtain about 15 mg of total RNA. An Oligotex-dT30 <Super> (Nihon Roche) was used to prepare Poly A RNA from this total RNA following the procedure recommended by the manufacturer, and about 150 μg of Poly A RNA was obtained.

cDNA was synthesized from 5 μg of this Poly A RNA by reverse transcription. The first strand of cDNA was synthesized using a TimeSaver cDNA Synthesis Kit (Pharmacia) with Oligo(dT)12–18 as the primer, following the procedure recommended by the manufacturer. An EcoRI adapter was attached to both ends of the synthesized cDNA.

EcoRI was added to 25 μl of the obtained cDNA solution for digestion, 4 μl (0.5 μg/μl) of dephosphorylated γgt11 (Lambda gt11/EcoRI/CIAP-treated: Stratagene) was added, a 1/20 volume of 3 M sodium acetate buffer solution (pH 5.2) and a 2.5-fold volume of ethanol were added, and the mixture was allowed to stand at −20° C. for one hour to precipitate the DNA. After centrifugation with a refrigeratd microcentrifuge at 15,000 rpm, 4° C. for 10 minutes, the supernatant was discarded and the pellet was collected.

In order to wash the DNA, 75% ethanol was added and after centrifugation at 15,000 rpm, 4° C. for 3 minutes the supernatant was discarded and the pellet was air-dried. The DNA pellet was dissolved in 8 μl of sterilized distilled water, and 1 μl of a 10×T4 DNA ligase buffer solution (300 mM Tris-HCl, pH 7.8, 100 mM MgCl$_2$, 100 mM DTT, 10 mM ATP) and 1 μl of T4 DNA ligase (Pharmacia) were added for a 3 hour ligation reaction at 16° C., to incorporate the cDNA into γgt11.

An in vitro packaging reaction was then conducted to prepare phage. The reaction was conducted from 4 μl of ligation reaction solution using a Gigapack II Gold Kit (Stratagene), following the procedure recommended by the manufacturer.

After completion of the reaction, the phage titer was measured. A portion of the packaging reaction solution was used to infect *E. coli* strain Y1090 which had been cultured in maltose-added NZY medium (10 g/l NZ amine, 5 g/l yeast extract, 5 g/l NaCl, 2 g/l MgSO$_4$·7H$_2$O) and resuspended in 10 mM MgSO$_4$ to OD600=1.0. As a result, the phage present in the packaging reaction solution was found to have an infectivity of 9.0×10$^6$ pfu/ml.

Example 5

Construction of Probe cDNA was synthesized from 200 ng of the Poly A RNA separated from fetal calf esophageal tissue, using randern hexamer and an RNA PCR Kit (Takara Shuzo) following the procedure recommended by the manufacturer.

This first strand cDNA was used to construct a probe by the polymerase chain reaction (PCR). The PCR primer was designed from the amino acid sequence of CAAF1, and the following degenerate primers P7S1 (sense primer: corresponding to LEDHLEG) and P7A1 (antisense primer: corresponding to AHIDIHK) were synthesized:

P7S1: 5'TT(A/C/G/T)GA(A/G)GA(C/T)CA(C/T)(C/T)T(A/C/G/ (SEQ ID NO: 8)
T)GA(A/G)GG-3'

P7A1: 5'TT(A/G)TG(A/G/T)AT(A/G)TC(A/G/T)AT(A/G)TG (SEQ ID NO: 9)
(A/C/G/T)GC-3'

One nmole of each of the primers from the first strand cDNA was used in a PCR reaction. The PCR reaction was conducted using a DNA Thermal Cycler (Perkin-Elmer/Cetus), with 30 cycles of reaction at 94° C. for 1 minute, 48° C. for 2 minutes and 72° C. for 2 minutes.

The amplified PCR product was subjected to electrophoresis in a 4% agarose gel (FMC Bioproducts: NuSieve GTG 3:1), and a DNA fragment anticipated to be 263 bp was cut out of the gel. This DNA fragment was purified using a Gene Clean Kit (Bio 101), and recovered in 10 µl of TE solution (10 mM Tris-HCl (pH 7.5), 1 mM EDTA).

A ligation reaction was performed with 5 µl of the DNA fragment solution and 1 µl of pTZ18R vector (Pharmacia, 50 ng/µl) digested with the restriction endonuclease SmaI, using a DNA Ligation Kit (Takara Shuzo) according to the procedure recommended by the manufacturer, to incorporate the cDNA into the pTZ18R vector.

E. coli strain JM109 (Toyobo) was transformed with 5 µl of this vector solution according to the method of Hanahan (DNA cloning: A practical approach (ed. D. M. Glover), vol.1, P.109-, IRC Press, (1985)). The cells were seeded onto L-amp plates containing X-gal, and the white colonies were selected out, thus selecting colonies which were ampicillin-resistant and lacking β-galactosidase.

The selected clones were cultured in a 2×YT-amp medium (1.6% bacto-trypton, 1% yeast extract, 0.5% NaCl, 100 µg/ml ampicillin), and a Magic Prep DNA Miniprep Kit (Promega) was used to prepare DNA according to the procedure recommended by the manufacturer. The prepared DNA was reacted with USB Sequenase version 2.0 (U.S. Biochemicals) using M13M4 primer (Takara Shuzo) under the conditions recommended by the manufacturer. The reaction product was subjected to electrophoresis, and the nucleotide sequence of the DNA incorporated into the vector was determined to confirm that it contained the nucleotide sequence for CAAF1.

To 5 µl (1 µg/µl) of DNA of the obtained clones were added 2 µl of a 10×T buffer (330 mM Tris-acetate (pH 7.9), 100 mM magnesium acetate, 5 mM DTT, 660 mM potassium acetate), 2 µl of 0.1% BSA, 1 µl of SacI (10 U/µl: Takara Shuzo) and 1 µl of XbaI (10 U/µl: Takara Shuzo), the solution was adjusted to 20 µl with sterilized distilled water and reacted at 37° C. for one hour, after which the DNA was cut. The entire reaction, solution containing the DNA fragments was subjected to electrophoresis in a 4% agarose gel (FMC Bioproducts: NuSieve GTG 3:1), and an approximately 280 bp DNA fragment was cut out of the gel. This DNA fragment was purified using a Gene Clean Kit (Bio 101), and recovered in 10 µl of TE solution (10 mM Tris-HCl (pH 7.5), 1 mM EDTA).

Template DNA consisting of 3 µl (about 25 ng) of the DNA fragment solution was labelled with [α-$^{32}$P]dCTP (Amersham) using a Megaprime DNA labelling system (Amersham), following the procedure recommended by the manufacturer. After completion of the labelling, a Nick column (Pharmacia) was used to purify the labelled DNA, which was used as a $^{32}$P-labelled probe to isolate cDNA for CAAF1.

Example 6

Isolation of cDNA for CAAF1 and Determination of its Nucleotide Sequence

The cDNA library prepared from fetal calf esophagus was used to infect E. coli Y1090 cells which were then seeded at $1 \times 10^4$ plaques per 90 mm dish. Twenty of the 90 mm dishes were prepared, to form about $2.0 \times 10^5$ plaques. The formed plaques were transferred to a Hybond-N membrane (Amersham), the membrane was treated for 2 minutes with a solution containing 0.5 M NaOH and 0.5 M NaCl and for 5 minutes with a solution containing 0.5 M Tris-HCl (pH 7.5) and 0.5 M NaCl, and then washed thoroughly with 0.1×SSC and 0.1 M ammonium acetate and air-dried on filter paper.

The membrane surface binding the plaque DNA was treated with UV to crosslink the DNA onto the membrane, and incubated at 42° C. for 2 hours in a prehybridization solution (6×SSC, 5×Denhardt's solution, 20 mM Tris-HCl (pH 7.5), 50% formamide, 0.5% SDS, 100 µg/ml denatured salmon sperm DNA) for blocking. The prehybridization solution was discarded, and to a fresh prehybridization solution was added a $^{32}$P-labelled probe denatured to single strands by rapid cooling after treatment at 96° C. for 5 minutes, and the membrane was immersed therein and incubated at 42° C. overnight for hybridization.

The membrane was washed with a solution containing 2×SSC, 0.5% SDS at room temperature for 15 minutes and at 42° C. for 15 minutes, then with a solution containing 0.5×SSC, 0.1% SDS at 42° C. for 15 minutes, and then with a solution of the same composition at 42° C. for 15 minutes. This was placed in a cassette with exposure film, exposed at −80° C. for 24 hours, and developed.

The plaques at the spot in which hybridized signals were detected were collected, plaques were formed in the same manner, and the plaques were isolated.

Thus were obtained 12 phage clones containing the target DNA fragment. Of these, the 3 phage clones γP7/32, γP7/34 and γP7/51 were used to infect E. coli Y1090, and high-titer phage solutions were obtained by the plate/lysate method.

A Lambda TRAPPLUS DNA Isolation Kit (CLONTEC) was used to purify about 10 µg of phage DNA from 10 ml of phage solution, following the procedure recommended by the manufacturer.

The incorporated DNA was amplified from this phage DNA by the PCR using λgt11 primers. The λgt11 primer (forward) and λgt11 primer (reverse) (Takara Shuzo) listed below were added in an amount of 1 µl (1 nmole/µl) each to 1 µl (1 ng/µl) of the phage DNA, and 10 µl of a 10×PCR buffer (100 mM Tris-HCl (pH 8.3), 500 mM KCl, 15 mM MgCl$_2$, 0.01% gelatin), 10 µl of 2 mM dNTP and 0.5 µl of Taq DNA polymerase (5 U/µl: Takara Shuzo) were added with sterilized distilled water to make 100 µl. The PCR reaction was conducted using a DNA Thermal Cycler (Perkin-Elmer/Cetus), with 30 cycles of reaction at 94° C. for 1 minute, 55° C. for 2 minutes and 72° C. for 2 minutes.

λgt11 primer (forward): 5'-GGTGGCGACGACTCCTGGAGCCCG-3' (SEQ ID NO: 10) λgt11 primer (reverse): 5'-TTGACACCAGACCAACTGGTAATG-3' (SEQ ID NO: 11)

The amplified PCR product was subjected to electrophoresis in a 4% agarose gel (FMC Bioproducts: NuSieve GTG 3:1), and DNA fragments derived from the phage clones λP7/32, λP7/34 and λP7/51 (about 600 bp, 550 bp and 450 bp) were cut out of the gel. The DNA fragments were purified using a Gene Clean Kit (Bio 101), and recovered in 10 μl of TE solution (10 mM Tris-HCl (pH 7.5), 1 mM EDTA). The DNA fragments were incorporated by a ligation reaction into the vector pTZ18R (Pharmacia) digested with the restriction endonuclease SmaI, using a DNA Ligation Kit (Takara Shuzo) according to the procedure recommended by the manufacturer.

E. coli strain JM109 (Toyobo) was transformed with 5 μl of the vector solutions according to the method of Hanahan (DNA cloning: A practical approach (ed. D. M. Glover), vol.1, P.109-, IRC Press, (1985)). The cells were seeded onto L-amp plates containing X-gal, and the white colonies were selected out, thus selecting colonies which were ampicillin-resistant and lacking β-galactosidase.

The selected colonies were cultured in a 2×YT-amp medium (1.6% bacto-trypton, 1% yeast extract, 0.5% NaCl, 100 μg/ml ampicillin), and a Magic Prep DNA Miniprep Kit (Promega) was used to prepare DNA according to the procedure recommended by the manufacturer. The plasmid DNAs were named pTZ/BP7-32, pTZ/BP7-34 and pTZ/BP7-51, respectively.

A 5 μg portion of each plasmid DNA, pTZ/BP7-32, pTZ/BP7-34 and pTZ/BP7-51 was reacted by USB Sequenase version 2.0 (U.S. Biochemicals) using M13M4 primer and M13MRV primer (Takara Shuzo) according to the method recommended by the manufacturer. The reaction product was subjected to electrophoresis in an acrylamide gel for sequencing, to determine the nucleotide sequence.

The lengths of the nucleotide sequences of pTZ/BP7-32, pTZ/BP7-34 and pTZ/BP7-51 were 602 bp, 562 bp and 448 bp, respectively, and their overlapping portions matched. The entire nucleotide sequence of 429 bp determined from the overlapping portions is listed as Sequence No.1 and in FIGS. 1, 2.

From this nucleotide sequence, the amino acid sequence of CAAF1 which is the primary translation product, i.e. the amino acid sequence before possible posttranslational modification, is deduced. This amino acid sequence minus the N-terminal methionine residue correspond to the amino acid sequence of the CAAF1 isolated from bovine amniotic fluid.

Example 7

Preparation of Monoclonal Antibodies with Binding Affinity to CAAF1

Female BALB/c mice were intraperitoneally immunized with 1–2 μg of the purified CAAF1 with Freund's complete adjuvant. The mice were then intraperitoneally immunized with 1 μg of CAAF1 with Freund's incomplete adjuvant twice at 3 week intervals thereafter. At one week after the final immunization, blood was taken from the caudal vein, and the blood antibody titers against CAAF1 were estimated by RIA described below. The mice with the highest blood antibody titers were selected and intravenously injected with 1 μg of CAAF1.

After 3 days, the spleens were extracted and the spleen cells were washed with RPMI1640 medium, and then mixed in a proportion of 5:1 with SP2/O Ag14 myeloma cells which had been washed in the same manner. The medium was removed by centrifugation, 1 ml of 50% polyethylene glycol was added to the cell pellet while stirring gently and RPMI1640 medium was added slowly for dilution, for cell fusion. After washing the cells, they were suspended in RPMI1640 medium containing 10% fetal calf serum and hypoxanthine/aminopterin/thymine (HAT), and dispensed into a 96-well microplate at 200 μl/well.

After 10 days of culturing at 37° C. in the presence of 5% $CO_2$ gas, the presence or absence of anti-CAAF1 antibodies in the culture supernatants was determined by RIA as described below. Hybridoma cells producing anti-CAAF1 antibodies were cloned by the limiting dilution method, and anti-CAAF1 antibody-producing hybridoma cell lines were established.

Of the monoclonal antibodies thus obtained, the 4 clones CAAF1-16-5, CAAF1-22-5, CAAF1-25-25 and CAAF1-31-5 were used in the following experiment.

The subtypes of the antibodies were determined with a mouse monoclonal antibody Isotyping Kit (Amersham). It was found as a result that CAAF1-16-5, CAAF1-22-5 and CAAF1-31-5 were $IgG_1$ and CAAF-1-25-25 was $IgG_{2a}$.

The hybridoma cells were transplanted into the peritoneal of RALB/c mice at about $10^7$ cells per mouse, and the ascites fluid produced after 1–2 weeks was collected.

The monoclonal antibodies in the ascites fluid were purified by affinity chromatography using a column with Protein A-Binding Sepharose (Pharmacia). The ascites fluid was diluted 3-fold with a buffer solution containing 3 M NaCl and 1.5 M glycine-HCl (pH 8.9), and after filtration it was applied a column filled with Protein A-Sepharose CL-4B (Pharmacia) which had been equilibrated with the same buffer solution, to bind the antibodies. The monoclonal antibodies were eluted out by 0.1 M citrate buffer (pH 6.0) for the $IgG_1$ monoclonal antibodies and 0.1 M citrate buffer (pH 5.0) for the $IgG_{2b}$ monoclonal antibodies. The fractions contained the antibodies at a purity of about 90% or greater, as estimated by SDS-PAGE.

The antibodies with binding affinity to CAAF1 were detected by radioimmunoassay (RIA) using purified CAAF1. The RIA was performed in the following manner. Rabbit anti-mouse IgG antibody (Immunobiology Research Laboratory) diluted to 10 μg/ml with PBS was added to a 96-well microplate (Xenobind) at 50 μl/well for coating. After washing with PBS containing 0.05% Tween20 (T-PBS), blocking of the wells was effected with a solution containing 3% bovine serum albumin (BSA). After washing 3 times in the same manner, 50 μl of a sample such as mouse antiserum or hybridoma culture supernatant was added and reacted therewith for one hour at room temperature.

After washing 3 times, PBS containing about 5000 cpm of $^{125}$I-labelled CAAF1 ($^{125}$I-CAAF1) and 3% BSA was added to each well and reacted therewith for one hour at room temperature. After washing 4 times, the $^{125}$I-CAAF1 binding to the antibodies from the sample was released with 10% acetic acid, and the radioactivity in the solution was measured with a gamma counter.

The $^{125}$I-CAAF1 was prepared by reacting purified CAAF1 with [$^{125}$I]-NaI using a Iodogen (Pierce), and separating the unreacted portion by gel filtration in a column filled with Sephadex-G25 (Pharmacia). This is the method described in the manual by Pierce Co.

Example 8

Detection of CAAF1 in Tissue by Immunohistological Staining

In order to detect CAAF1 protein in fetal calf tissue and excised human tissue, the CAAF1 protein was immunohistochemically stained using a HISTOFINE immunohistochemical staining system (Nichirei). The fetal calf tissues listed in Tables 1 and 2, and excised human tissue, were fixed in a 15% formalin buffer solution and embedded in paraffin. After removing the slices from the paraffin, they were treated for 20 minutes with methanol containing 3% hydrogen peroxide to eliminate the intrinsic peroxidase activity.

After additional blocking with blocking reagent II (10% normal rabbit serum), CAAF1-22-5 hybridoma ascites fluid, diluted 1000-fold with PBS containing 3% BSA, was used as a primary antibody and reacted with each of the slices at room temperature for 2 hours. After 5-minute washing with PBS 3 times, they were reacted with a secondary antibody (biotin-labelled rabbit anti-mouse IgM+IgA+IgG antibody, 10 μg/ml) at room temperature for one hour. After 5-minute washing with PBS 3 times, they were further reacted with an enzyme reagent (peroxidase-labelled streptoavidin, 100 μg/ml) at room temperature for 30 minutes. After 5-minute washing with PBS 3 times, they were finally reacted with the peroxidase substrate diaminobentidine, and the presence of CAAF1 was visually determined.

Photographs showing the results are provided in FIGS. 8 to 13. The presence or absence of reaction is indicated in Tables 1 and 2.

With fetal calves, expression of CAAF1 protein was confirmed in epithelial tissue such as esophagus, skin and cornea and in lymphatic tissue such as spleen and thymus. Of the epithelial tissue, all squamous epithelial cells except for basal cells were positive, and in the blood and lymphatic tissues, neutrophils and macrophages were positive.

TABLE 1

Reactivity of anti-CAAF1 antibody with various tissues Immunoreactivity

| Central nervous system | | |
|---|---|---|
| Cerebrum | – | |
| Cerebellum | – | |
| Brain stem | – | |
| Spinal cord | – | |
| Cardiovascular system | | |
| Aorta | – | |
| Vena cava | – | |
| Heart | – | |
| Lymphatic tissue | | |
| Thymus | ++ | Hassall body, macrophage, PMN |
| Spleen | +++ | Macrophage, PMN |
| Digestive system | | |
| Parotid gland | – | |
| Submaxilla | – | |
| Esophagus | +++ | Epithelium/platycytes |
| Stomach | – | |
| Duodenum | – | |
| Jejenum | – | |
| Colon | – | |
| Liver | – | |
| Pancreas | – | |
| Respiratory system | | |
| Trachea | + | Epithelium/ciliated and non-cilated epithelial cells |
| Lungs | – | |

TABLE 2

Reactivity of anti-CAAF1 antibody with various tissues Immunoreactivity

| Urinary system | | |
|---|---|---|
| Kidneys | – | |
| Urinary duct | – | |
| Bladder | – | |
| Genitals | | |
| Gonads | – | |
| Endocrine organs | | |
| Pituitary gland | – | |
| Adrenal gland | – | |
| Skin | | |
| Skin | +++ | Cuticle/keratinous cells |
| Sensory organs | | |
| Eye/cornea | +++ | Epithelium/platycytes |
| Eye/tunica conjuctiva | +++ | Epithelium/platycytes |
| Other | | |
| Hematopoietic cells | +++ | Macrophage, PMN |
| Placenta | +++ | Amniotic membrane/platycytes |
| Umbilical cord | +++ | Amniotic membrane/platycytes |

(PMN: Polymorphonuclear leukocytes)

Of normal human tissue, CAAF1 protein immunoreactivity was confirmed and squamous epithelial cells were positive in mucosal epithelial tissue such as the esophagus and cervix. In the blood and lymphatic tissue, the neutrophils and macrophages were positive. However, of the normal human mucosal epithelial tissue such as the esophagus and cervix in which CAAF1 protein immunoreactivity was confirmed, the atypical epithelial cells were negative. Hyperexpression was confirmed in cancerous areas of those tissues with a tendency to cornification. Expression was also confirmed in cancerous areas of lungs and skin in which no CAAF1 protein immunoreactivity had been found when normal, and hyperexpression was confirmed in those tissues with pulmonary squamous-cell carcinoma with a strong tendency to cornification, squamous carcinoma of the skin, Bowen's disease (intraepithelial carcinoma) and senile keratosis (intraepithelial carcinoma). Furthermore, neutrophils and macrophages infiltrating the lesion sites exhibited strong CAAF1 protein immunoreactivity.

The existence of antigen reacting with CAAF1-22-5 monoclonal antibody in human tissue strongly suggests the existence in human tissue of a protein (human CAAF1) homologous with bovine CAAF1. Also, the differences of cancer cells and normal cells in immunoreactivities against the anti-CAAF1 antibody suggest the usefulness of the anti-CAAF1 antibody as a diagnostic agent for cancer (particularly squamous-cell carcinoma of the skin, oral cavity, esophagus, respiratory organs and cervix). In addition, the immunoreactivity of neutrophils and macrophages against anti-CAAF1 antibody further suggests additional usefulness of the anti-CAAF1 antibody as a diagnostic agent for various inflammatory diseases.

Example 9

Assay of CAAF1 in Amniotic Fluid and Serum

The anti-CAAF1 monoclonal antibody CAAF1-22-5 was dissolved in a 50 mM sodium bicarbonate buffer at pH 9.6, to a concentration of 10 μg/ml. This solution was dispensed in an ELISA plate (NUNC) at 100 μl/well and incubated at 4° C. overnight for coating of the monoclonal antibodies. After blocking with HBS (0.15 M NaCl, 20 mM HEPES-Na pH 7.4) containing 1% ovalbumin, a standard substance and the specimens were appropriately diluted with HBS containing 0.5% OVA and 0.05% Tween20 (OVA-T-HBS), and 100 μl thereof was added for reaction at room temperature for one hour.

After washing of the wells with HBS containing 0.05% Tween20 by a Plate Washer (Biotech), there was added 100 μl of OVA-T-HBS containing 1 μg/ml of biotin-labelled CAAF1-22-5 monoclonal antibody or biotin-labelled CAAF1-25-25 monoclonal antibody, for reaction at room temperature for one hour. After washing the wells, 100 μl of a horseradish peroxidase-labelled avidin D (vector) solution diluted 5000-fold with OVA-T-HBS was added thereto for reaction at room temperature for one hour. The wells were again washed, and then 100 μl of a solution containing o-phenylenediamine and hydrogen peroxide was added and a color development reaction was conducted at room temperature for 30 minutes. After stop of the reaction with 100 μl of 2 N sulfuric acid, stop the absorbance of each of the wells at 492 nm was measured with a microplate reader.

The above-mentioned biotin-labelled monoclonal antibodies were prepared in the following manner. A 2 mg portion of purified monoclonal antibody from each of the 4 clones, CAAF1-16-5, CAAF1-22-5, CAAF1-25-25 and CAAF1-31-5 was dissolved in 2 ml of 0.1 M borate buffer (pH 8.8), and after dialysis against the same buffer, 450 μg of NHS-LC-Biotin (Pierce) was added and allowed to react therewith at 4° C. overnight. This was dialyzed against PBS, and the unreacted reagent was removed.

CAAF1 purified from bovine amniotic fluid was used as the standard substance, and the CAAF1 concentrations in the specimens were calculated from the calibration curve (FIG. 6).

With this assay system, it was possible to measure CAAF1 with a minimum detectable limit of about 10 pg/ml when using biotin-labelled CAAF1-25-25 monoclonal antibody and about 500 pg/ml when using biotin-labelled CAAF1-22-5 monoclonal antibody. Amniotic fluid from cows in the 4th month of pregnancy contained about 1 μg/ml of CAAF1 and bovine serum contained 20–60 ng/ml. No significant reaction was observed when biotin-labelled CAAF1-25-25 monoclonal antibody was used as opposed to a human specimen. When biotin-labelled CAAF1-22-5 monoclonal antibody was used, CAAF1 was measured at 20–200 ng/ml in normal human serum and at 2–5 ng/ml in human amniotic fluid.

These results demonstrate that the present invention allows measurement of CAAF1 immunoreactivity in bovine and human body fluids. The fact that antigen reacting with CAAF1 22-5 monoclonal antibody was found to be present in human blood and amniotic fluid, strongly suggests the presence in human blood and amniotic fluid of a protein homologous with bovine CAAF1 (human CAAF1).

The results of the above-mentioned immunohistological staining which confirmed strong CAAF1 immunoreactivity of cancer cells (particularly squamous-cell carcinoma of the skin, esophagus, respiratory organs and cervix) as compared with normal cells, and the ability to measure CAAF1 immunoreactivity in human body fluids using anti-CAAF1 antibody, suggests the usefulness of this assay system for the diagnosis of cancer (particularly squamous-cell carcinoma of the skin, esophagus, respiratory organs and cervix). Also, the strong CAAF1 immunoreactivity of neutrophils and macrophages resulting from the above-mentioned immunohistological staining further suggests the usefulness of this CAAF1 assay system for the diagnosis of various inflammatory diseases.

Example 10

Construction of Probe

From the DNA sequence of bovine CAAF1 was selected a sequence in the domain of the EF-hand motif believed to be highly conserved among species, and the following primers, BP7/242-261 (sense primer) and BP7/408-389 (antisense primer) were synthesized as PCR primers. BP7/242-261: 5'-ATCATCAACATCTTCCACCA-3' (SEQ ID NO: 13) BP7/408-389: 5'-TCTTTATCGGCATCCAGGTC-3' (SEQ ID NO: 14)

These primers were used for RT-PCR with an RNA PCR Kit (Takara Shuzo) from 50 ng of Poly A RNA extracted from human peripheral neutrophils and cultured human epidermal cells (Krabow) (cultured for 48 hours after addition of serum). After reverse transcription of the Poly A RNA, 3 μl (10 pmole/μl) of each primer was added to 10 ul of cDNA solution, and 10 μl of a 10×PCR buffer (100 mM Tris-HCl (pH 8.3), 500 mM KCl, 15 mM MgCl$_2$, 0.01% gelatin), 10 μl of 2 mM DNTP and 0.5 μl of Taq DNA polymerase (5 U/μl: Takara Shuzo) were added with sterilized distilled water to make 100 μl. The PCR reaction was conducted using a DNA Thermal Cycler (Perkin-Elmer/Cetus), with 35 cycles of reaction at 94° C. for 1 minute, 48° C. for 2 minutes and 72° C. for 2 minutes.

The anticipated PCR product of approximately 170 bp was amplified from all of the samples. After electrophoresis of the DNA fragments from human peripheral neutrophils with 4% agarose gel (FMC Bioproducts: NuSieve GTG3:1), they were purified using a Marmade Gene Clean Kit (Bio 101) and recovered in 10 μl of TE solution (10 mM Tris-HCl (pH 7.5), 1 mM EDTA).

A 5 μl portion of each DNA fragment solution was ligated to pMOSBlue vector using a pMOSBlue T-vector Kit (Amersham), and E. coli strain JM109 (Toyobo) was transformed with 5 μl of the vector solution according to the method of Hanahan (DNA cloning: A practical approach (ed. D. M. Glover), vol.1, p.109-, IRC Press, (1985)). The cells were seeded onto L-amp plates containing X-gal, and the white colonies were selected out, thus selecting colonies which were ampicillin-resistant and lacking β-galactosidase.

The selected clones were cultured in a 2×YT-amp medium (1.6% bacto-trypton, 1% yeast extract, 0.5% NaCl, 100 μg/ml ampicillin), and a Wizard Prep DNA Miniprep Kit (Promega) was used to purify the plasmid DNA according to the procedure recommended by the manufacturer. The prepared DNA was reacted using an AutoRead Sequencing Kit (Pharmacia), under the conditions recommended by the manufacturer, and the nucleotide sequence was determined with an A.L.F.II DNA Sequencer (Pharmacia). The nucleotide sequence was confirmed to be about 80% homologous with the nucleotide sequence for bovine CAAF1.

In addition, the following primers, PMN.HP7S 1-15 and PMN.HP7A 126-112 were synthesized for the purpose of verifying the obtained nucleotide sequence, and an RT-PCR reaction was conducted from the above-mentioned Poly A RNA using an RNA PCR Kit (Takara Shuzo), with 35 cycles under reaction conditions of 94° C. for 1 minute, 50° C. for 1 minute and 72° C. for 2 minutes.

PMN.HP7S 1–15: 5'-TACTCAGTTCGGAAG-3' (SEQ ID NO: 15)

PMN.HP7A 126–112: 5'-TTGGAATATTTCATC-3' (SEQ ID NO: 16)

The anticipated PCR product of approximately 130 bp was amplified from all of the samples. After electrophoresis of the DNA fragments from human peripheral neutrophils with 4% agarose gel (FMC Bioproducts: NuSieve GTG3:1), they were purified using a Marmade Gene Clean Kit (Bio 101) and each DNA fragment was ligated to PCRII vector using a TA Cloning Kit (Invitrogen). *E. coli* strain JM109 (Toyobo) was transformed with 5μl of the vector solution according to the method of Hanahan (DNA cloning: A practical approach (ed. D. M. Glover), vol.1, p.109-, IRC Press, (1985)), the cells were seeded onto L-amp plates containing X-gal, and the white colonies were selected out, thus selecting colonies which were ampicillin-resistant and lacking β-galactosidase.

A selected clone pHP7/PMN was cultured in a 2×YT-amp medium (1.6% bacto-trypton, 1% yeast extract, 0.5% NaCl, 100 μg/ml ampicillin), and a Wizard Prep DNA Miniprep Kit (Promega) was used to purify the DNA according to the procedure recommended by the manufacturer. The prepared DNA was reacted using an AutoRead Sequencing Kit (Pharmacia), under the conditions recommended by the manufacturer, and the nucleotide sequence was determined with an A.L.P.II DNA Sequencer (Pharmacia). The nucleotide sequence was about 80% homologous with the nucleotide sequence for bovine CAAF1, and the overlapping portions matched exactly with the nucleotide sequence mentioned above.

A 2 μg portion of DNA of the obtained clone pHP7/PMN was cut by one hour reaction at 37° C. with EcoRI (20 U/μl: Takara Shuzo). All of the resulting DNA fragments were subjected to electrophoresis in a 4% agarose gel (FMC Bioproducts: NuSieve GTG3:1), and a DNA fragment of about 130 bp was cut out of the gel. This DNA fragment was purified using a Gene Clean Kit (Bio 101), and recovered in 10μl of TE solution (10 mM Tris-HCl (pH 7.5), 1 mM EDTA).

Template DNA consisting of 3 μl (about 25 ng) of the DNA fragment solution was labelled with [α-$^{32}$P]dCTP (Amersham) using a Megaprime DNA labelling system (Amersham), following the procedure recommended by the manufacturer. After completion of the labelling, a Nick column (Pharmacia) was used to purify the labelled DNA, which was used as a $^{32}$P-labelled probe to isolate cDNA for human CAAF1.

Example 11

Isolation of cDNA for Human CAAF1 and Determination of its Nucleotide Seauence

RNA was extracted from 0.5 g of adult human esophageal tissue using Isogen (Nippon Gene), to obtain about 1.5 mg of total RNA. An Oligotex-dT30 <Super> (Nihon Roche) was used to prepare Poly A RNA from this total RNA following the procedure recommended by the manufacturer, and about 50 μg of Poly A RNA was obtained.

cDNA was synthesized from 5 μg of this Poly A RNA using a TimeSaver cDNA Synthesis Kit (Pharmacia), according to the procedure recommended by the manufacturer. The primer used was NotI/Oligo(dT)18 primer (Directional Cloning Toolbox, Pharmacia). An EcoRI adapter was attached to both ends of the synthesized cDNA, and after phosphorylation and further addition of NotI for digestion, it was incorporated into dephosphorylated λExCell (λExCell NotI/EcoRI/CIP, Pharmacia).

An in vitro packaging reaction was then conducted using a Gigapack III Gold Kit (Stratagene), following the procedure recommended by the manufacturer. After completion of the reaction, a portion of the packaging reaction solution was used to infect *E. coli* strain NM522 which had been cultured in maltose-added NZY medium (10 g/l NZ amine, 5 g/l yeast extract, 5 g/l NaCl, 2 g/l MgSO$_4$·7H$_2$O) and resuspended in 10 mM MgSO$_4$ to OD600=2.0. As a result, the phage present in the packaging reaction solution was found to have an infectivity of 1.0×10$^6$ pfu/ml.

A cDNA library prepared from adult human esophagus was used to infect *E. coli* NM522 cells which were then seeded at 1×10$^4$ plaques per 90 mm dish. Twenty of the 90 mm dishes were prepared, to form about 2.0×10$^5$ plaques. The formed plaques were transferred to a Hybond-N$^+$ membrane (Amersham), the membrane was treated for 2 minutes with a solution containing 0.5 M NaOH and 0.5 M NaCl and for 5 minutes with a solution containing 0.5 M Tris-HCl (pH 7.5) and 0.5 M NaCl, and then washed thoroughly with 0.1×SSC and 0.1 M ammonium acetate and air-dried on filter paper.

The membrane surface binding the plaque DNA was treated with UV to crosslink the DNA onto the membrane. The membrane was incubated at 42° C. for 2 hours in a prehybridization solution (6×NET, 0.2×Blotto, 50% formamide, 0.5% SDS, 200 μg/ml denatured salmon sperm DNA) for blocking. The prehybridization solution was discarded, and to a fresh prehybridization solution (5×NET, 0.1×Blotto, 30% formamide, 0.4% SDS, 10% dextran sulfate, 200 μg/ml denatured salmon sperm DNA) was added a $^{32}$P-labelled probe denatured to single strands by rapid cooling after treatment at 96° C. for 5 minutes, and the membrane was immersed therein and incubated at 42° C. overnight for hybridization.

The membrane was washed with a solution containing 2×SSC, 0.5% SDS at room temperature for 15 minutes, with a solution of the same composition at 50° C. for 15 minutes, then with a solution containing 0.5×SSC, 0.1% SDS at 50° C. for 15 minutes, and then with a solution of the same composition at 50° C. for 15 minutes. This was placed in a cassette with exposure film, exposed at −80° C. for 24 hours, and developed.

The plaques at the spot in which hybridized signals were detected were collected, plaques were formed in the same manner, and the plaques were isolated. Thus was obtained a single phage clone λExCell/HP7/ESO310 containing the target DNA fragment.

The phage clone λExCell/HP7/ESO310 was used to infect *E. coli* NP66 to release phagmid pExCell/HP7/ESO310 in vivo from λExCell/HP7/ESO310, and it was then separated and recovered using a Wizard Prep DNA Miniprep Kit (Promega). The purified pExCell/HP7/ESO310 was then infected into *E. coli* JM109 (Toyobo) to transform it. The cells were seeded onto L-amp plates containing X-gal, and the white colonies were selected out, thus selecting colonies which were ampicillin-resistant and lacking β-galactosidase.

The selected colonies were cultured together with helper phage VCSM-13 (Stratagene) in a 2×YT-amp medium (1.6% bacto-trypton, 1% yeast extract, 0.5% NaCl, 100 μg/ml ampicillin, 40 mg/ml kanamycin), and a Wizard M13 DNA Miniprep Kit (Promega) was used to purify the single-stranded DNA according to the procedure recommended by the manufacturer.

A 2 μg portion of the single-stranded DNA of pExCell/HP7/ESO310 was reacted using an AutoRead Sequencing Kit (Pharmacia), under the conditions recommended by the manufacturer, and the nucleotide sequence was determined with an A.L.F.II DNA Sequencer (Pharmacia). The sequence was confirmed to be about 73% homologous with the nucleotide sequence for bovine CAAF1, and the overlapping portions matched exactly with the nucleotide sequence of pHP7/PMN mentioned above.

In addition, the following primers were synthesized for the purpose of verifying the obtained nucleotide sequence, and an RT-PCR reaction was conducted from 100 ng of adult human esophageal Poly A RNA. The first strand cDNA was synthesized using a Ready-to-GO T-Primed First-Strand Kit (Pharmacia), following the procedure recommended by the manufacturer. The PCR was conducted with 35 cycles of reaction at 94° C. for 1 minute, 60° C. for 1 minute and 72° C. for 1 minute.

HP7S 7-26: 5'-ACATTAGGCTGGGAAGATGA-3' (SEQ ID NO: 17)

HP7A 336-317: 5'-GGACATTGCTGGGTAAAAAG-3' (SEQ ID NO: 18)

As a result, the anticipated PCR product of approximately 330 bp was amplified, and after electrophoresis with a 4% agarose gel (FMC Bioproducts: NuSieve GTG3:1), the DNA fragment was purified and incorporated into a PCR Script vector (Stratagene) which had been digested with restriction endonuclease SmaI. E. coli JM109 (Toyobo) was transformed with this vector pHP7/ESO, and the cells were seeded onto L-amp plates containing X-gal and the white colonies were selected out, thus selecting colonies which were ampicillin-resistant and lacking β-galactosidase.

The selected clones were cultured together with helper phage VCSM-13 (Stratagene) in a 2×YT-amp medium (1.6% bacto-trypton, 1% yeast extract, 0.5% NaCl, 100 µg/ml ampicillin, 40 µg/ml kanamycin), and a Wizard M13 DNA Miniprep Kit (Promega) was used to purify the single-stranded DNA according to the procedure recommended by the manufacturer.

A 2 µg portion of the single-stranded DNA of pHP7/ESO was reacted using an AutoRead Sequencing Kit (Pharmacia), under the conditions recommended by the manufacturer, and the nucleotide sequence was determined with an A.L.F.II DNA Sequencer (Pharmacia). The overlapping sequences matched exactly with the nucleotide sequence of pExCell/HP7/ESO310 mentioned above.

Meanwhile, human neutrophil-derived Poly A RNA was used for RT-PCR in the same manner and the nucleotide sequence was determined, to confirm the nucleotide sequence of pExCell/HP7/ESO310.

The first strand cDNA was synthesized from 100 ng of adult human neutrophils using a TaKaRa RNA PCR Kit (Takara Shuzo), following the procedure recommended by the manufacturer. The PCR was conducted using the above-mentioned HP7S 7-26 and HP7A 336-317 as primers, with 35 cycles of reaction at 94° C. for 1 minute, 58° C. for 1 minute and 72° C. for 2 minutes.

As a result, the anticipated PCR product of approximately 330 bp was amplified. A portion thereof was subjected to electrophoresis with a 4% agarose gel (FMC Bioproducts: NuSieve GTG Agarose), and the DNA fragment was recovered from the gel and purified. The DNA fragment was incorporated into a PCRII vector (Stratagene) using a TA Cloning Kit (Invitrogen) according to the procedure recommended by the manufacturer, and E. coli JM109 (Toyobo) was transformed with the vector. The cells were seeded onto an L-amp plate containing X-gal and the white colonies were selected out, thus selecting colonies which were ampicillin-resistant and lacking β-galactosidase.

The selected colonies were cultured in a 2×YT-amp medium (1.6% bacto-trypton, 1% yeast extract, 0.5% NaCl, 100 µg/ml ampicillin, 40 µg/ml kanamycin), and a Wizard Minipreps DNA Purification System (Promega) was used to prepare DNA according to the procedure recommended by thea manufacturer. This plasmid DNA was named pHP7/NEU.

A 10 µg portion of the pHP7/NEU DNA was reacted using an AutoRead Sequencing Kit (Pharmacia), under the conditions recommended by the manufacturer, and the nucleotide sequence of the DNA incorporated into the vector was determined with an A.L.F.II DNA Sequencer (Pharmacia). The overlapping portions of the sequence matched exactly with the nucleotide sequence of pExCell/HP7/ESO310 mentioned above.

RT-PCR was conducted in the same manner for human keratinocytes, and upon determining the nucleotide sequence of the amplified product, the overlapping portions thereof matched exactly with the nucleotide sequence of pExCell/HP7/ESO310.

The entire determined nucleotide sequence is shown in SEQ ID NO: 12.

From this nucleotide sequence, the amino acid sequence of human CAAF1 is deduced which is the primary translation product, i.e. the amino acid sequence before possible posttranslational modification.

---

What is claimed is:

1. An isolated or purified calcium-binding protein comprising an amino acid sequence listed in SEQ ID NO: 19 or 20.

2. A fused protein comprising a protein according to claim 1 and another protein.

\* \* \* \* \*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH:  429
      (B) TYPE:  nucleic acid
      (C) STRANDEDNESS:  double
      (D) TOPOLOGY: linear (ii) MOLECULE TYPE:  cDNA (x) PUBLICATION INFORMATION:
    (K) RELEVANT RESIDUES IN SEQ ID NO:1: FROM 1 TO 429

(xi) SEQUENCE DESCRIPTION:SEQ ID NO:1:

```
CTGGCATTCC ACACTTCTGT GCAGAGGGGT GAACGTAGTT TGGTAAA ATG ACT           53
                                                   Met Thr
                                                     1

AAG CTG GAA GAT CAC CTG GAG GGA ATC ATC AAC ATC TTC CAC CAG TAC     101
Lys Leu Glu Asp His Leu Glu Gly Ile Ile Asn Ile Phe His Gln Tyr
      5               10                  15

TCC GTT CGG GTG GGG CAT TTC GAC ACC CTC AAC AAG CGT GAG CTG AAG     149
Ser Val Arg Val Gly His Phe Asp Thr Leu Asn Lys Arg Glu Leu Lys
 20              25                  30

CAG CTG ATC ACA AAG GAA CTT CCC AAA ACC CTC CAG AAC ACC AAA GAT     197
Gln Leu Ile Thr Lys Glu Leu Pro Lys Thr Leu Gln Asn Thr Lys Asp
 35              40                  45                  50

CAA CCT ACC ATT GAC AAA ATA TTC CAA GAC CTG GAT GCC GAT AAA GAC     245
Gln Pro Thr Ile Asp Lys Ile Phe Gln Asp Leu Asp Ala Asp Lys Asp
                 55                  60                  65

GGA GCC GTC AGC TTT GAG GAA TTC GTA GTC CTG GTG TCC AGG GTG CTG     293
Gly Ala Val Ser Phe Glu Glu Phe Val Val Leu Val Ser Arg Val Leu
             70                  75                  80

AAA ACA GCC CAC ATA GAT ATC CAC AAA GAG TAGGAA GCTCTTTCCA           339
Lys Thr Ala His Ile Asp Ile His Lys Glu
             85                  90

GCAATGTCCC CAAGAAGACT TACCCTTCTC CTCCCTGAGG CTGCCTTACC CGAGGGAAGA   399

GAGAATTAAT AAACGTACTT TGGCAAAGTT                                    429
```

(2) INFORMATION FOR SEQ ID NO:2:

(i) SEQUENCE CHARACTERISTICS:
        (A) LENGTH: 51
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:2: FROM 1 TO 51

(xi) SEQUENCE DESCRIPTION:SEQ ID NO:2:

```
Thr Lys Leu Glu Asp His Leu Glu Gly Ile Ile Asn Ile Phe His Gln
 1               5                  10                  15

Tyr Ser Val Arg Val Gly His Phe Asp Thr Leu Asn Lys Arg Glu Leu
             20                  25                  30

Lys Gln Leu Ile Thr Lys Glu Leu Pro Lys Thr Leu Gln Asn Thr Lys
         35                  40                  45

Asp Gln Pro
 50
```

(2) INFORMATION FOR SEQ ID NO:3:

(i) SEQUENCE CHARACTERISTICS:
        (A) LENGTH:  8
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:3: FROM 1 TO 8

(xi) SEQUENCE DESCRIPTION:SEQ ID NO:3:

Ile Phe Gln Asp Leu Asp Ala Asp (2) INFORMATION FOR SEQ ID NO:4:

(i) SEQUENCE CHARACTERISTICS:
        (A) LENGTH: 12
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:4: FROM 1 TO 12

(xi) SEQUENCE DESCRIPTION:SEQ ID NO:4:

```
Asp Gly Ala Val Ser Phe Glu Glu Phe Val Val Leu
1               5                   10
```

(2) INFORMATION FOR SEQ ID NO:5:

(i) SEQUENCE CHARACTERISTICS:
        (A) LENGTH: 9
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:5: FROM 1 TO 9

(xi) SEQUENCE DESCRIPTION:SEQ ID NO:5:

```
Thr Ala His Ile Asp Ile His Lys Glu
1               5
```

(2) INFORMATION FOR SEQ ID NO:6:

(i) SEQUENCE CHARACTERISTICS:
        (A) LENGTH: 31
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:6: FROM 1 TO 31

(xi) SEQUENCE DESCRIPTION:SEQ ID NO:6:

```
Leu Pro Lys Thr Leu Gln Asn Thr Lys Asp Gln Pro Thr Ile Asp Lys
1               5                   10                  15
Ile Phe Gln Asp Leu Asp Ala Asp Lys Asp Gly Ala Val Ser Phe
                20                  25                  30
```

(2) INFORMATION FOR SEQ ID NO:7:

(i) SEQUENCE CHARACTERISTICS:
        (A) LENGTH: 20
        (B) TYPE: amino acid
        (C) STRANDEDNESS:
        (D) TOPOLOGY:linear (x) PUBLICATION INFORMATION:
        (K) RELEVANT RESIDUES IN SEQ ID NO:7:FROM 1 TO 20

(xi) SEQUENCE DESCRIPTION:SEQ ID NO:7:

```
Glu Phe Val Val Leu Val Ser Arg Val Leu Lys Thr Ala His Ile Asp
1               5                   10                  15
Ile His Lys Glu
                20
```

(2) INFORMATION FOR SEQ ID NO:8:

(i) SEQUENCE CHARACTERISTICS:
        (A) LENGTH: 20
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:8: FROM 1 TO 20

(xi) SEQUENCE DESCRIPTION:SEQ ID NO:8:

TTNGARGAYC AYYTNGARGG                                               20

(2) INFORMATION FOR SEQ ID NO:9:

(i) SEQUENCE CHARACTERISTICS:
        (A) LENGTH: 20
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:9:FROM 1 TO 20

(xi) SEQUENCE DESCRIPTION:SEQ ID NO:9:

TTRTGDATRT CDATRTGNGC                                               20

(2) INFORMATION FOR SEQ ID NO:10:

(i) SEQUENCE CHARACTERISTICS:
        (A) LENGTH: 24
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:10: FROM 1 TO 24

(xi) SEQUENCE DESCRIPTION:SEQ ID NO:10:

GGTGGCGACG ACTCCTGGAG CCCG                                          24

(2) INFORMATION FOR SEQ ID NO:11:

(i) SEQUENCE CHARACTERISTICS:
        (A) LENGTH: 24
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:11: FROM 1 TO 24

(xi) SEQUENCE DESCRIPTION:SEQ ID NO:11:

TTGACACCAG ACCAACTGGT AATG                                          24

(2) INFORMATION FOR SEQ ID NO:12:

(i) SEQUENCE CHARACTERISTICS:
        (A) LENGTH: 441
        (B) TYPE: nucleic acid
        (C) STRANDEDNESS:double
        (D) TOPOLOGY:linear (ii) MOLECULE TYPE: cDNA (x) PUBLICATION INFORMATION:
    (K) RELEVANT RESIDUES IN SEQ ID NO:12: FROM 1 TO 441

(xi) SEQUENCE DESCRIPTION:SEQ ID NO:12:

```
GGTTAACATT AGGCTGGGAA G ATG ACA AAA CTT GAA GAG CAT CTG GAG GGA            51
                       Met Thr Lys Leu Glu Glu His Leu Glu Gly
                                    5                       10

ATT GTC AAT ATC TTC CAC CAA TAC TCA GTT CGG AAG GGG CAT TTT GAC            99
Ile Val Asn Ile Phe His Gln Tyr Ser Val Arg Lys Gly His Phe Asp
                15                  20                  25

ACC CTC TCT AAG GGT GAG CTG AAG CAG CTG CTT ACA AAG GAG CTT GCA           147
Thr Leu Ser Lys Gly Glu Leu Lys Gln Leu Leu Thr Lys Glu Leu Ala
            30                  35                  40

AAC ACC ATC AAG AAT ATC AAA GAT AAA GCT GTC ATT GAT GAA ATA TTC           195
Asn Thr Ile Lys Asn Ile Lys Asp Lys Ala Val Ile Asp Glu Ile Phe
        45                  50                  55

CAA GGC CTG GAT GCT AAT CAA GAT GAA CAG GTC GAC TTT CAA GAA TTC           243
Gln Gly Leu Asp Ala Asn Gln Asp Glu Gln Val Asp Phe Gln Glu Phe
    60                  65                  70

ATA TCC CTG GTA GCC ATT GCG CTG AAG GCT GCC CAT TAC CAC ACC CAC           291
Ile Ser Leu Val Ala Ile Ala Leu Lys Ala Ala His Tyr His Thr His
75                  80                  85                  90

AAA GAG TAGGTAGCTC TCTGAAGGCT TTTTACCCAG CAATGTCCTC AATGAGGGTC            347
Lys Glu

TTTTCTTTCC CTCACCAAAA CCCAGCCTTG CCCGTGGGGA GTAAGAGTTA ATAAACACAC         407

TCACGAAAAG TTAAAAAAAA AAAAAAAAAA TTCT                                     441
```

(2) INFORMATION FOR SEQ ID NO:13:

(i) SEQUENCE CHARACTERISTICS:
        (A) LENGTH: 20
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:13:  FROM 1 TO 20

(xi) SEQUENCE DESCRIPTION:SEQ ID NO:13:

```
ATCATCAACA TCTTCCACCA                                                      20
```

(2) INFORMATION FOR SEQ ID NO:14:

(i) SEQUENCE CHARACTERISTICS:
        (A) LENGTH: 20
        (B) TYPE: nucleic acid
        (C) STRANDEDNESS:single
        (D) TOPOLOGY:linear (ii) MOLECULE TYPE: synthetic (x) PUBLICATION INFORMATION:
        (K) RELEVANT RESIDUES IN SEQ ID NO:14: FROM 1 TO 20

(xi) SEQUENCE DESCRIPTION:SEQ ID NO:14:

```
TCTTTATCGG CATCCAGGTC                                                      20
```

(2) INFORMATION FOR SEQ ID NO:15:

(i) SEQUENCE CHARACTERISTICS:
        (A) LENGTH: 15
        (B) TYPE: nucleic acid
        (C) STRANDEDNESS:single (D) TOPOLOGY:linear (ii) MOLECULE TYPE: synthetic (x) PUBLICATION INFORMATION:
             (K) RELEVANT RESIDUES IN SEQ ID NO:15: FROM 1 TO 15

(xi) SEQUENCE DESCRIPTION:SEQ ID NO:15:

TACTCAGTTC GGAAG                                                     15

(2) INFORMATION FOR SEQ ID NO:16:

(i) SEQUENCE CHARACTERISTICS:
             (A) LENGTH: 15
             (B) TYPE: nucleic acid
             (C) STRANDEDNESS:single
             (D) TOPOLOGY:linear (ii) MOLECULE TYPE: synthetic (x) PUBLICATION INFORMATION:
             (K) RELEVANT RESIDUES IN SEQ ID NO:16: FROM 1 TO 15

(xi) SEQUENCE DESCRIPTION:SEQ ID NO:16:

TTGGAATATT TCATC                                                     15

(2) INFORMATION FOR SEQ ID NO:17:

(i) SEQUENCE CHARACTERISTICS:
             (A) LENGTH: 20
             (B) TYPE: nucleic acid
             (C) STRANDEDNESS:single
             (D) TOPOLOGY:linear (ii) MOLECULE TYPE: synthetic (x) PUBLICATION INFORMATION:
             (K) RELEVANT RESIDUES IN SEQ ID NO:17: FROM 1 TO 20

(xi) SEQUENCE DESCRIPTION:SEQ ID NO:17:

ACATTAGGCT GGGAAGATGA                                                20

(2) INFORMATION FOR SEQ ID NO:18:

(i) SEQUENCE CHARACTERISTICS:
             (A) LENGTH: 20
             (B) TYPE: nucleic acid
             (C) STRANDEDNESS:single
             (D) TOPOLOGY:linear (ii) MOLECULE TYPE: synthetic (x) PUBLICATION INFORMATION:
             (K) RELEVANT RESIDUES IN SEQ ID NO:18: FROM 1 TO 20

(xi) SEQUENCE DESCRIPTION:SEQ ID NO:18:

GGACATTGCT GGGTAAAAAG                                                20

(2) INFORMATION FOR SEQ ID NO:19:

(i) SEQUENCE CHARACTERISTICS:
             (A) LENGTH: 92
             (B) TYPE:  amino acid
             (C) STRANDEDNESS:
             (D) TOPOLOGY:linear (ii) MOLECULE TYPE:  cDNA (x) PUBLICATION INFORMATION:
             (K) RELEVANT RESIDUES IN SEQ ID NO:19: FROM 1 TO 92

-continued (xi) SEQUENCE DESCRIPTION:SEQ ID NO:19:

```
Met Thr Lys Leu Glu Asp His Leu Glu Gly Ile Ile Asn Ile Phe His
                 5                  10                  15

Gln Tyr Ser Val Arg Val Gly His Phe Asp Thr Leu Asn Lys Arg Glu
             20                  25                  30

Leu Lys Gln Leu Ile Thr Lys Glu Leu Pro Lys Thr Leu Gln Asn Thr
         35                  40                  45

Lys Asp Gln Pro Thr Ile Asp Lys Ile Phe Gln Asp Leu Asp Ala Asp
     50                  55                  60

Lys Asp Gly Ala Val Ser Phe Glu Glu Phe Val Val Leu Val Ser Arg
65                  70                  75                  80

Val Leu Lys Thr Ala His Ile Asp Ile His Lys Glu
                 85                  90
```

(2) INFORMATION FOR SEQ ID NO:20:

(i) SEQUENCE CHARACTERISTICS:
        (A) LENGTH:92
        (B) TYPE: amino acid
        (C) STRANDEDNESS:
        (D) TOPOLOGY:linear (ii) MOLECULE TYPE: cDNA (x) PUBLICATION INFORMATION:
        (K) RELEVANT RESIDUES IN SEQ ID NO:20: FROM 1 TO 92

(xi) SEQUENCE DESCRIPTION:SEQ ID NO:20:

```
                        Met Thr Lys Leu Glu Glu His Leu Glu Gly
                                     5                  10

Ile Val Asn Ile Phe His Gln Tyr Ser Val Arg Lys Gly His Phe Asp
             15                  20                  25

Thr Leu Ser Lys Gly Glu Leu Lys Gln Leu Leu Thr Lys Glu Leu Ala
         30                  35                  40

Asn Thr Ile Lys Asn Ile Lys Asp Lys Ala Val Ile Asp Glu Ile Phe
         45                  50                  55

Gln Gly Leu Asp Ala Asn Gln Asp Glu Gln Val Asp Phe Gln Glu Phe
     60                  65                  70

Ile Ser Leu Val Ala Ile Ala Leu Lys Ala Ala His Tyr His Thr His
75                  80                  85                  90

Lys Glu
```